(12) United States Patent
Giachelli et al.

(10) Patent No.: US 7,794,742 B2
(45) Date of Patent: Sep. 14, 2010

(54) DEVICES FOR PROMOTING EPITHELIAL CELL DIFFERENTIATION AND KERATINIZATION

(75) Inventors: Cecilia Maria Giachelli, Mill Creek, WA (US); Benjamin Leo Beckstead, Seattle, WA (US)

(73) Assignee: University of Washington, Seattle, WA (US)

( * ) Notice: Subject to any disclaimer, the term of this patent is extended or adjusted under 35 U.S.C. 154(b) by 520 days.

(21) Appl. No.: 11/054,369

(22) Filed: Feb. 8, 2005

(65) Prior Publication Data

US 2006/0177479 A1 Aug. 10, 2006

(51) Int. Cl.
*A61K 38/17* (2006.01)
*A61F 2/00* (2006.01)
*A61M 25/00* (2006.01)

(52) U.S. Cl. .................... 424/426; 514/12; 600/435
(58) Field of Classification Search ................ None
See application file for complete search history.

(56) References Cited

U.S. PATENT DOCUMENTS

| | | | |
|---|---|---|---|
| 5,798,115 A * | 8/1998 | Santerre et al. ............. | 424/423 |
| 6,048,964 A | 4/2000 | Lee et al. | |
| 6,337,387 B1 | 1/2002 | Sakano et al. | |
| 6,706,289 B2 | 3/2004 | Lewis et al. | |
| 2002/0151487 A1 | 10/2002 | Nickoloff et al. | |
| 2003/0083465 A1 | 5/2003 | Zimrin et al. | |
| 2004/0077962 A1* | 4/2004 | Kroll ......................... | 600/513 |
| 2004/0137569 A1 | 7/2004 | Chan et al. | |
| 2005/0220886 A1* | 10/2005 | Bodmer et al. ............. | 424/489 |

FOREIGN PATENT DOCUMENTS

WO     WO 00/25809     *  5/2000

OTHER PUBLICATIONS

Brooker et al., Notch ligands with constrasting functions:jagged1 and delta1 in the mouse ear, 2006, Development, vol. 133, pp. 1277-1286.*
Notch signaling in the integrated control of keratinocyte growth/differentiation and tumor suppression, 2004, Seminars in Cancer Biology, vol. 14, pp. 374-386.*
Defective intracellular transport and processing of JAG1 missense mutations in Alagille syndrome, 2001, Human Molecular Genetics, vol. 10, Issue 4, pp. 405-413.*
Shimizu et al., Mouse jagged1 physically interacts with Notch2 and other Notch receptors, 1999, Journal of Biological Chemistry, vol. 274, Issue 46, pp. 32961-32969.*
Bork et al., Go hunting in sequence databases but watch out for the traps, 1996, Trends in Genetics, vol. 12, pp. 425-427.*
Bork, Powers and Pitfalls in Sequence Analysis: the 70% hurdle, 2000, Genome Research, vol. 10, pp. 398-400.*
Brenner, Errors in genome annotation, 1999, Trends in Genetics, vol. 15, pp. 132-132.*
Doerks et al., Protein annotation: detective work for function prediction, 1998, Trends in Genetics, vol. 14, pp. 248-250.*
Ngo et al., The protein folding problem and tertiary structure prediction,1994, pp. 492-495.*
Skolnick et al., From genes to protein structure and function: novel applications of computational approaches in the genomic era, 2000, Trends in Biotech, vol. 18, Issue 1, pp. 34-39.*
Smith et al., The challenge of genome sequence annotation or "the devil is in the details", 1997, Nature Biotechnology, vol. 15, pp. 1222-1223.*
Wells et al., Addivity of mutational effects in proteins, 1990, Biochemistry, vol. 29, pp. 8509-8517.*
Gray, G.E., et al., "Human Ligands of the Notch Receptor," *American Journal of Pathology* 154(3):785-794, Mar. 1999.
Hicks, C., et al., "A Secreted Delta1-Fc Fusion Protein Functions Both As an Activator and Inhibitor of Notch1 Signaling," *Journal of Neuroscience Research Journal* 68(6):655-667, published online May 6, 2002.
Karanu, F.N., et al., "The Notch Ligand Jagged-1 Represents a Novel Growth Factor of Human Hematopoietic Stem Cells," *J. Exp. Med.* 192(9):1365-1372, Nov. 6, 2000.
Lai, Eric C., "Notch Signaling: Control of Cell Communication and Cell Fate," *Development* 131:965-973, 2004.
Mumm, J.S. and R. Koppan, "Notch Signaling: From the Outside In," *Developmental Biology* 228:151-165, 2000.
Rangarajan, A., et al., "Notch Signaling is a Direct Determinant of Keratinocyte Growth Arrest and Entry Into Differentiation," *The EMBO Journal* 20(13):3427-3436, 2001.
Shimizu, K., et al., "Binding of Delta1, Jagged1, and Jagged2 to Notch2 Rapidly Induces Cleavage, Nuclear Translocation, and Hyperphosphorylation of Notch2," *Molecular and Cellular Biology*, pp. 6913-6922, Sep. 2000.
Shimizu, K., et al., "Mouse Jagged1 Physically Interacts with Notch2 and Other Notch Receptors," *Journal of Biological Chemistry* 274(46):32961-32969, Nov. 12, 1999.
Weinmaster, G., "The Ins and Outs of Notch Signaling," *Molecular and Cellular Neuroscience* 9:91-102, 1997.

* cited by examiner

*Primary Examiner*—Robert Landsman
*Assistant Examiner*—Ian Dang
(74) *Attorney, Agent, or Firm*—Christensen O'Connor Johnson Kindness PLLC

(57) ABSTRACT

In one aspect, the present invention provides a biomaterial having at least one biocompatible surface. The biocompatible surface comprises a plurality of immobilized Notch ligand molecules, wherein the plurality of immobilized Notch ligand molecules are capable of promoting differentiation in one or more epithelial cells. In another aspect, the present invention provides an implantable medical device comprising a layer of a biomaterial. Another aspect of the invention provides methods for promoting epithelial cell differentiation. The methods of this aspect of the invention include the step of contacting one or more epithelial cells with a biomaterial comprising an amount of immobilized Notch ligand molecules sufficient to promote differentiation in the one or more epithelial cells.

5 Claims, 13 Drawing Sheets

| | | SEQ ID NO:2 |
|---|---|---|
| rJagged-1.DSL | VTCDDHYYGFGCNKFCRPRDDFFGHYACDQNGNKTCMEGWMGPEC | SEQ ID NO:2 |
| hJagged-1.DSL | VTCDDYYYGFGCNKFCRPRDDFFGHYACDQNGNKTCMEGWMGPEC | SEQ ID NO:4 |
| hJagged-2.DSL | VRCDENYYSATCNKFCRPRNDFFGHYTCDQYGNKACMDGWMGKEC | SEQ ID NO:6 |
| hDelta-1.DSL | FVCDEHYYGEGCSVFCRPRDDAFGHFTCGERGEKVCNPGWKGPYC | SEQ ID NO:8 |
| Consensus.DSL | XXCDXXYXXXCXXFCRPRXDXFGHXXCXXXGXKXCXXGWXGXXC | SEQ ID NO:9 |

*Fig.1B.*

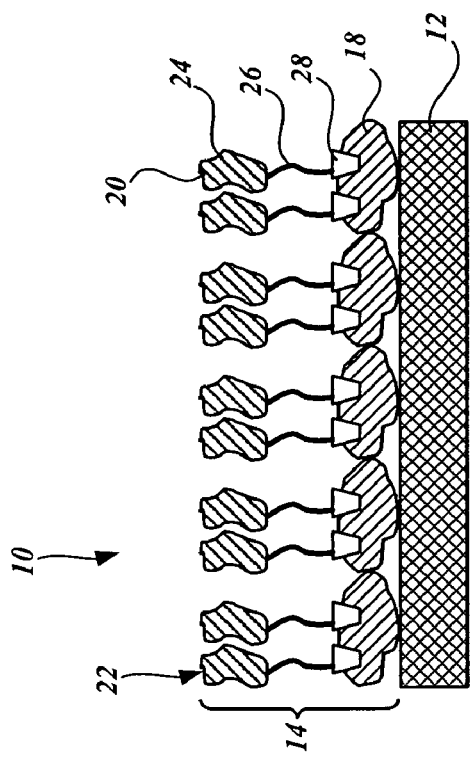
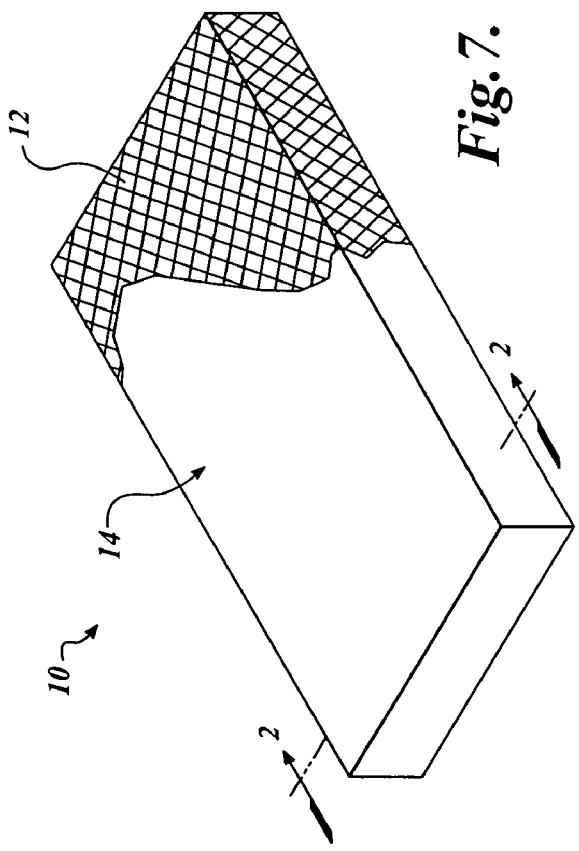
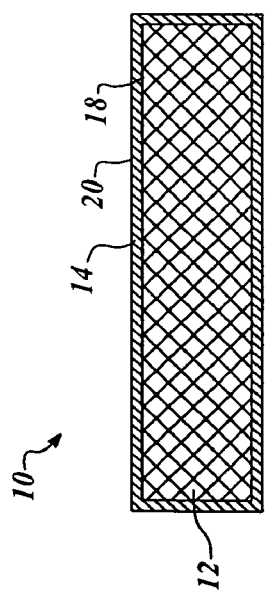

SEQUENCE LISTING

```
<160> NUMBER OF SEQ ID NOS: 9

<210> SEQ ID NO 1
<211> LENGTH: 1068
<212> TYPE: PRT
<213> ORGANISM: Rattus norvegicus

<400> SEQUENCE: 1

Met Arg Ser Pro Arg Thr Arg Gly Arg Pro Gly Arg Pro Leu Ser Leu
1               5                   10                  15

Leu Leu Ala Leu Leu Cys Ala Leu Arg Ala Lys Val Cys Gly Ala Ser
            20                  25                  30

Gly Gln Phe Glu Leu Glu Ile Leu Ser Met Gln Asn Val Asn Gly Glu
        35                  40                  45

Leu Gln Asn Gly Asn Cys Cys Ala Glu Pro Gly Thr Leu Val Arg Pro
    50                  55                  60

Tyr Lys Cys Thr Arg Asp Glu Cys Asp Thr Tyr Phe Lys Val Cys Leu
65                  70                  75                  80

Lys Glu Tyr Gln Ser Arg Val Thr Ala Gly Gly Pro Cys Ser Phe Gly
            85                  90                  95

Ser Gly Ser Thr Pro Val Ile Gly Gly Asn Thr Phe Asn Leu Lys Ala
            100                 105                 110

Ser Arg Gly Asn Asp Arg Asn Arg Ile Val Leu Pro Phe Ser Phe Ala
        115                 120                 125

Trp Pro Arg Ser Tyr Thr Leu Leu Val Glu Ala Trp Asp Ser Ser Asn
    130                 135                 140

Asp Thr Ile Gln Pro Asp Ser Ile Ile Glu Lys Ala Ser His Ser Gly
145                 150                 155                 160

Met Ile Asn Pro Ser Arg Gln Trp Gln Thr Leu Lys Gln Asn Thr Gly
                165                 170                 175

Ile Ala His Phe Glu Tyr Gln Ile Arg Val Thr Cys Asp Asp His Tyr
            180                 185                 190

Tyr Gly Phe Gly Cys Asn Lys Phe Cys Arg Pro Arg Asp Asp Phe Phe
```

-continued

```
            195                 200                 205
Gly His Tyr Ala Cys Asp Gln Asn Gly Asn Lys Thr Cys Met Glu Gly
            210                 215                 220
Trp Met Gly Pro Glu Cys Asn Lys Ala Ile Cys Arg Gln Gly Cys Ser
225                 230                 235                 240
Pro Lys His Gly Ser Cys Lys Leu Pro Gly Asp Cys Arg Cys Gln Tyr
                245                 250                 255
Gly Trp Gln Gly Leu Tyr Cys Asp Lys Cys Ile Pro His Pro Gly Cys
                260                 265                 270
Val His Gly Thr Cys Asn Glu Pro Trp Gln Cys Leu Cys Glu Thr Asn
            275                 280                 285
Trp Gly Gly Gln Leu Cys Asp Lys Asp Leu Asn Tyr Cys Gly Thr His
            290                 295                 300
Gln Pro Cys Leu Asn Arg Gly Thr Cys Ser Asn Thr Gly Pro Asp Lys
305                 310                 315                 320
Tyr Gln Cys Ser Cys Pro Glu Gly Tyr Ser Gly Pro Asn Cys Glu Ile
                325                 330                 335
Ala Glu His Ala Cys Leu Ser Asp Pro Cys His Asn Arg Gly Ser Cys
            340                 345                 350
Lys Glu Thr Ser Ser Gly Phe Glu Cys Glu Cys Ser Pro Gly Trp Thr
            355                 360                 365
Gly Pro Thr Cys Ser Thr Asn Ile Asp Asp Cys Ser Pro Asn Asn Cys
            370                 375                 380
Ser His Gly Gly Thr Cys Gln Asp Leu Val Asn Gly Phe Lys Cys Val
385                 390                 395                 400
Cys Pro Pro Gln Trp Thr Gly Lys Thr Cys Gln Leu Asp Ala Asn Glu
                405                 410                 415
Cys Glu Ala Lys Pro Cys Val Asn Ala Arg Ser Cys Lys Asn Leu Ile
                420                 425                 430
Ala Ser Tyr Tyr Cys Asp Cys Leu Pro Gly Trp Met Gly Gln Asn Cys
            435                 440                 445
Asp Ile Asn Ile Asn Asp Cys Leu Gly Gln Cys Gln Asn Asp Ala Ser
            450                 455                 460
Cys Arg Asp Leu Val Asn Gly Tyr Arg Cys Ile Cys Pro Pro Gly Tyr
465                 470                 475                 480
Ala Gly Asp His Cys Glu Arg Asp Ile Asp Glu Cys Ala Ser Asn Pro
                485                 490                 495
Cys Leu Asn Gly Gly His Cys Gln Asn Glu Ile Asn Arg Phe Gln Cys
                500                 505                 510
Leu Cys Pro Thr Gly Phe Ser Gly Asn Leu Cys Gln Leu Asp Ile Asp
            515                 520                 525
Tyr Cys Glu Pro Asn Pro Cys Gln Asn Gly Ala Gln Cys Tyr Asn Arg
            530                 535                 540
Ala Ser Asp Tyr Phe Cys Lys Cys Pro Glu Asp Tyr Glu Gly Lys Asn
545                 550                 555                 560
Cys Ser His Leu Lys Asp His Cys Arg Thr Thr Pro Cys Glu Val Ile
                565                 570                 575
Asp Ser Cys Thr Val Ala Met Ala Ser Asn Asp Thr Pro Glu Gly Val
                580                 585                 590
Arg Tyr Ile Ser Ser Asn Val Cys Gly Pro His Gly Lys Cys Lys Ser
            595                 600                 605
Glu Ser Gly Gly Lys Phe Thr Cys Asp Cys Asn Lys Gly Phe Thr Gly
            610                 615                 620
```

-continued

```
Thr Tyr Cys His Glu Asn Ile Asn Asp Cys Glu Gly Asn Pro Cys Thr
625                 630                 635                 640

Asn Gly Gly Thr Cys Ile Asp Gly Val Asn Ser Tyr Lys Cys Ile Cys
                    645                 650                 655

Ser Asp Gly Trp Glu Gly Ala His Cys Glu Asn Asn Ile Asn Asp Cys
                660                 665                 670

Ser Gln Asn Pro Cys His Tyr Gly Gly Thr Cys Arg Asp Leu Val Asn
                675                 680                 685

Asp Phe Tyr Cys Asp Cys Lys Asn Gly Trp Lys Gly Lys Thr Cys His
690                 695                 700

Ser Arg Asp Ser Gln Cys Asp Glu Ala Thr Cys Asn Asn Gly Gly Thr
705                 710                 715                 720

Cys Tyr Asp Glu Val Asp Thr Phe Lys Cys Met Cys Pro Gly Gly Trp
                725                 730                 735

Glu Gly Thr Thr Cys Asn Ile Ala Arg Asn Ser Ser Cys Leu Pro Asn
                740                 745                 750

Pro Cys His Asn Gly Gly Thr Cys Val Val Asn Gly Asp Ser Phe Thr
            755                 760                 765

Cys Val Cys Lys Glu Gly Trp Glu Gly Pro Ile Cys Thr Gln Asn Thr
770                 775                 780

Asn Asp Cys Ser Pro His Pro Cys Tyr Asn Ser Gly Thr Cys Val Asp
785                 790                 795                 800

Gly Asp Asn Trp Tyr Arg Cys Glu Cys Ala Pro Gly Phe Ala Gly Pro
                805                 810                 815

Asp Cys Arg Ile Asn Ile Asn Glu Cys Gln Ser Ser Pro Cys Ala Phe
                820                 825                 830

Gly Ala Thr Cys Val Asp Glu Ile Asn Gly Tyr Gln Cys Ile Cys Pro
            835                 840                 845

Pro Gly His Ser Gly Ala Lys Cys His Glu Val Ser Gly Arg Ser Cys
    850                 855                 860

Ile Thr Met Gly Arg Val Ile Leu Asp Gly Ala Lys Trp Asp Asp Asp
865                 870                 875                 880

Cys Asn Thr Cys Gln Cys Leu Asn Gly Arg Val Ala Cys Ser Lys Val
                885                 890                 895

Trp Cys Gly Pro Arg Pro Cys Arg Leu His Lys Gly His Gly Glu Cys
                900                 905                 910

Pro Asn Gly Gln Ser Cys Ile Pro Val Leu Asp Asp Gln Cys Phe Val
            915                 920                 925

Arg Pro Cys Thr Gly Ala Gly Glu Cys Arg Ser Ser Ser Leu Gln Pro
    930                 935                 940

Val Lys Thr Lys Cys Thr Ser Asp Ser Tyr Tyr Gln Asp Asn Cys Ala
945                 950                 955                 960

Asn Ile Thr Phe Thr Phe Asn Lys Glu Met Met Ser Pro Gly Leu Thr
                965                 970                 975

Thr Glu His Ile Cys Ser Glu Leu Arg Asn Leu Asn Ile Leu Lys Asn
            980                 985                 990

Val Ser Ala Glu Tyr Ser Ile Tyr  Ile Ala Cys Glu Pro  Ser Leu Ser
        995                 1000                 1005

Ala Asn  Asn Glu Ile His Val  Ala Ile Ser Ala Glu  Asp Ile Arg
    1010                 1015                 1020

Asp Asp  Gly Asn Pro Val Lys  Glu Ile Thr Asp Lys  Ile Ile Asp
    1025                 1030                 1035
```

```
Leu Val Ser Lys Arg Asp Gly Asn Ser Ser Leu Ile Ala Ala Val
    1040                1045                1050

Ala Glu Val Arg Val Gln Arg Arg Pro Leu Lys Asn Arg Thr Asp
    1055                1060                1065

<210> SEQ ID NO 2
<211> LENGTH: 45
<212> TYPE: PRT
<213> ORGANISM: Artificial Sequence
<220> FEATURE:
<223> OTHER INFORMATION: Peptide from Rattus norvegicus

<400> SEQUENCE: 2

Val Thr Cys Asp Asp His Tyr Tyr Gly Phe Gly Cys Asn Lys Phe Cys
1               5                   10                  15

Arg Pro Arg Asp Asp Phe Phe Gly His Tyr Ala Cys Asp Gln Asn Gly
                20                  25                  30

Asn Lys Thr Cys Met Glu Gly Trp Met Gly Pro Glu Cys
            35                  40                  45

<210> SEQ ID NO 3
<211> LENGTH: 1067
<212> TYPE: PRT
<213> ORGANISM: Homo sapiens

<400> SEQUENCE: 3

Met Arg Ser Pro Arg Thr Arg Gly Arg Ser Gly Arg Pro Leu Ser Leu
1               5                   10                  15

Leu Leu Ala Leu Leu Cys Ala Leu Arg Ala Lys Val Cys Gly Ala Ser
                20                  25                  30

Gly Gln Phe Glu Leu Glu Ile Leu Ser Met Gln Asn Val Asn Gly Glu
                35                  40                  45

Leu Gln Asn Gly Asn Cys Cys Gly Gly Ala Arg Asn Pro Gly Asp Arg
        50                  55                  60

Lys Cys Thr Arg Asp Glu Cys Asp Thr Tyr Phe Lys Val Cys Leu Lys
65                  70                  75                  80

Glu Tyr Gln Ser Arg Val Thr Ala Gly Gly Pro Cys Ser Phe Gly Ser
                85                  90                  95

Gly Ser Thr Pro Val Ile Gly Gly Asn Thr Phe Asn Leu Lys Ala Ser
                100                 105                 110

Arg Gly Asn Asp Arg Asn Arg Ile Val Leu Pro Phe Ser Phe Ala Trp
            115                 120                 125

Pro Arg Ser Tyr Thr Leu Leu Val Glu Ala Trp Asp Ser Ser Asn Asp
    130                 135                 140

Thr Val Gln Pro Asp Ser Ile Ile Glu Lys Ala Ser His Ser Gly Met
145                 150                 155                 160

Ile Asn Pro Ser Arg Gln Trp Gln Thr Leu Lys Gln Asn Thr Gly Val
                165                 170                 175

Ala His Phe Glu Tyr Gln Ile Arg Val Thr Cys Asp Asp Tyr Tyr Tyr
                180                 185                 190

Gly Phe Gly Cys Asn Lys Phe Cys Arg Pro Arg Asp Asp Phe Phe Gly
            195                 200                 205

His Tyr Ala Cys Asp Gln Asn Gly Asn Lys Thr Cys Met Glu Gly Trp
    210                 215                 220

Met Gly Pro Glu Cys Asn Arg Ala Ile Cys Arg Gln Gly Cys Ser Pro
225                 230                 235                 240

Lys His Gly Ser Cys Lys Leu Pro Gly Asp Cys Arg Cys Gln Tyr Gly
```

-continued

```
                245                 250                 255
Trp Gln Gly Leu Tyr Cys Asp Lys Cys Ile Pro His Pro Gly Cys Val
            260                 265                 270
His Gly Ile Cys Asn Glu Pro Trp Gln Cys Leu Cys Glu Thr Asn Trp
            275                 280                 285
Gly Gly Gln Leu Cys Asp Lys Asp Leu Asn Tyr Cys Gly Thr His Gln
            290                 295                 300
Pro Cys Leu Asn Gly Gly Thr Cys Ser Asn Thr Gly Pro Asp Lys Tyr
305                 310                 315                 320
Gln Cys Ser Cys Pro Glu Gly Tyr Ser Gly Pro Asn Cys Glu Ile Ala
            325                 330                 335
Glu His Ala Cys Leu Ser Asp Pro Cys His Asn Arg Gly Ser Cys Lys
            340                 345                 350
Glu Thr Ser Leu Gly Phe Glu Cys Glu Cys Ser Pro Gly Trp Thr Gly
            355                 360                 365
Pro Thr Cys Ser Thr Asn Ile Asp Asp Cys Ser Pro Asn Asn Cys Ser
            370                 375                 380
His Gly Gly Thr Cys Gln Asp Leu Val Asn Gly Phe Lys Cys Val Cys
385                 390                 395                 400
Pro Pro Gln Trp Thr Gly Lys Thr Cys Gln Leu Asp Ala Asn Glu Cys
            405                 410                 415
Glu Ala Lys Pro Cys Val Asn Ala Lys Ser Cys Lys Asn Leu Ile Ala
            420                 425                 430
Ser Tyr Tyr Cys Asp Cys Leu Pro Gly Trp Met Gly Gln Asn Cys Asp
            435                 440                 445
Ile Asn Ile Asn Asp Cys Leu Gly Gln Cys Gln Asn Asp Ala Ser Cys
            450                 455                 460
Arg Asp Leu Val Asn Gly Tyr Arg Cys Ile Cys Pro Pro Gly Tyr Ala
465                 470                 475                 480
Gly Asp His Cys Glu Arg Asp Ile Asp Glu Cys Ala Ser Asn Pro Cys
            485                 490                 495
Leu Asn Gly Gly His Cys Gln Asn Glu Ile Asn Arg Phe Gln Cys Leu
            500                 505                 510
Cys Pro Thr Gly Phe Ser Gly Asn Leu Cys Gln Leu Asp Ile Asp Tyr
            515                 520                 525
Cys Glu Pro Asn Pro Cys Gln Asn Gly Ala Gln Cys Tyr Asn Arg Ala
            530                 535                 540
Ser Asp Tyr Phe Cys Lys Cys Pro Glu Asp Tyr Glu Gly Lys Asn Cys
545                 550                 555                 560
Ser His Leu Lys Asp His Cys Arg Thr Thr Pro Cys Glu Val Ile Asp
            565                 570                 575
Ser Cys Thr Val Ala Met Ala Ser Asn Asp Thr Pro Glu Gly Val Arg
            580                 585                 590
Tyr Ile Ser Ser Asn Val Cys Gly Pro His Gly Lys Cys Lys Ser Gln
            595                 600                 605
Ser Gly Gly Lys Phe Thr Cys Asp Cys Asn Lys Gly Phe Thr Gly Thr
            610                 615                 620
Tyr Cys His Glu Asn Ile Asn Asp Cys Glu Ser Asn Pro Cys Arg Asn
625                 630                 635                 640
Gly Gly Thr Cys Ile Asp Gly Val Asn Ser Tyr Lys Cys Ile Cys Ser
            645                 650                 655
Asp Gly Trp Glu Gly Ala Tyr Cys Glu Thr Asn Ile Asn Asp Cys Ser
            660                 665                 670
```

-continued

```
Gln Asn Pro Cys His Asn Gly Gly Thr Cys Arg Asp Leu Val Asn Asp
            675                 680                 685

Phe Tyr Cys Asp Cys Lys Asn Gly Trp Lys Gly Lys Thr Cys His Ser
    690                 695                 700

Arg Asp Ser Gln Cys Asp Glu Ala Thr Cys Asn Asn Gly Gly Thr Cys
705                 710                 715                 720

Tyr Asp Glu Gly Asp Ala Phe Lys Cys Met Cys Pro Gly Gly Trp Glu
                725                 730                 735

Gly Thr Thr Cys Asn Ile Ala Arg Asn Ser Ser Cys Leu Pro Asn Pro
                740                 745                 750

Cys His Asn Gly Gly Thr Cys Val Val Asn Gly Glu Ser Phe Thr Cys
            755                 760                 765

Val Cys Lys Glu Gly Trp Glu Gly Pro Ile Cys Ala Gln Asn Thr Asn
        770                 775                 780

Asp Cys Ser Pro His Pro Cys Tyr Asn Ser Gly Thr Cys Val Asp Gly
785                 790                 795                 800

Asp Asn Trp Tyr Arg Cys Glu Cys Ala Pro Gly Phe Ala Gly Pro Asp
                805                 810                 815

Cys Arg Ile Asn Ile Asn Glu Cys Gln Ser Ser Pro Cys Ala Phe Gly
                820                 825                 830

Ala Thr Cys Val Asp Glu Ile Asn Gly Tyr Arg Cys Val Cys Pro Pro
        835                 840                 845

Gly His Ser Gly Ala Lys Cys Gln Glu Val Ser Gly Arg Pro Cys Ile
    850                 855                 860

Thr Met Gly Ser Val Ile Pro Asp Gly Ala Lys Trp Asp Asp Asp Cys
865                 870                 875                 880

Asn Thr Cys Gln Cys Leu Asn Gly Arg Ile Ala Cys Ser Lys Val Trp
                885                 890                 895

Cys Gly Pro Arg Pro Cys Leu Leu His Lys Gly His Ser Glu Cys Pro
            900                 905                 910

Ser Gly Gln Ser Cys Ile Pro Ile Leu Asp Asp Gln Cys Phe Val His
        915                 920                 925

Pro Cys Thr Gly Val Gly Glu Cys Arg Ser Ser Ser Leu Gln Pro Val
    930                 935                 940

Lys Thr Lys Cys Thr Ser Asp Ser Tyr Tyr Gln Asp Asn Cys Ala Asn
945                 950                 955                 960

Ile Thr Phe Thr Phe Asn Lys Glu Met Met Ser Pro Gly Leu Thr Thr
                965                 970                 975

Glu His Ile Cys Ser Glu Leu Arg Asn Leu Asn Ile Leu Lys Asn Val
            980                 985                 990

Ser Ala Glu Tyr Ser Ile Tyr Ile Ala Cys Glu Pro Ser Pro Ser Ala
        995                 1000                1005

Asn Asn Glu Ile His Val Ala Ile Ser Ala Glu Asp Ile Arg Asp
    1010                1015                1020

Asp Gly Asn Pro Ile Lys Glu Ile Thr Asp Lys Ile Ile Asp Leu
    1025                1030                1035

Val Ser Lys Arg Asp Gly Asn Ser Ser Leu Ile Ala Ala Val Ala
    1040                1045                1050

Glu Val Arg Val Gln Arg Arg Pro Leu Lys Asn Arg Thr Asp
    1055                1060                1065

<210> SEQ ID NO 4
<211> LENGTH: 45
```

```
<212> TYPE: PRT
<213> ORGANISM: Artificial Sequence
<220> FEATURE:
<223> OTHER INFORMATION: Peptide from homo sapiens

<400> SEQUENCE: 4

Val Thr Cys Asp Asp Tyr Tyr Tyr Gly Phe Gly Cys Asn Lys Phe Cys
1               5                   10                  15

Arg Pro Arg Asp Asp Phe Phe Gly His Tyr Ala Cys Asp Gln Asn Gly
            20                  25                  30

Asn Lys Thr Cys Met Glu Gly Trp Met Gly Pro Glu Cys
        35                  40                  45

<210> SEQ ID NO 5
<211> LENGTH: 1067
<212> TYPE: PRT
<213> ORGANISM: Homo sapiens

<400> SEQUENCE: 5

Met Arg Ala Gln Gly Arg Gly Arg Leu Pro Arg Arg Leu Leu Leu Leu
1               5                   10                  15

Leu Ala Leu Trp Val Gln Ala Ala Arg Pro Met Gly Tyr Phe Glu Leu
            20                  25                  30

Gln Leu Ser Ala Leu Arg Asn Val Asn Gly Glu Leu Leu Ser Gly Ala
        35                  40                  45

Cys Cys Asp Gly Asp Gly Arg Thr Thr Arg Ala Gly Gly Cys Gly His
    50                  55                  60

Asp Glu Cys Asp Thr Tyr Val Arg Val Cys Leu Lys Glu Tyr Gln Ala
65                  70                  75                  80

Lys Val Thr Pro Thr Gly Pro Cys Ser Tyr Gly His Gly Ala Thr Pro
                85                  90                  95

Val Leu Gly Gly Asn Ser Phe Tyr Leu Pro Pro Ala Gly Ala Ala Gly
            100                 105                 110

Asp Arg Ala Arg Ala Arg Ala Gly Gly Asp Gln Asp Pro Gly
        115                 120                 125

Leu Val Val Ile Pro Phe Gln Phe Ala Trp Pro Arg Ser Phe Thr Leu
    130                 135                 140

Ile Val Glu Ala Trp Asp Trp Asp Asn Asp Thr Thr Pro Asn Glu Glu
145                 150                 155                 160

Leu Leu Ile Glu Arg Val Ser His Ala Gly Met Ile Asn Pro Glu Asp
                165                 170                 175

Arg Trp Lys Ser Leu His Phe Ser Gly His Val Ala His Leu Glu Leu
            180                 185                 190

Gln Ile Arg Val Arg Cys Asp Glu Asn Tyr Tyr Ser Ala Thr Cys Asn
        195                 200                 205

Lys Phe Cys Arg Pro Arg Asn Asp Phe Phe Gly His Tyr Thr Cys Asp
    210                 215                 220

Gln Tyr Gly Asn Lys Ala Cys Met Asp Gly Trp Met Gly Lys Glu Cys
225                 230                 235                 240

Lys Glu Ala Val Cys Lys Gln Gly Cys Asn Leu Leu His Gly Gly Cys
                245                 250                 255

Thr Val Pro Gly Glu Cys Arg Cys Ser Tyr Gly Trp Gln Gly Arg Phe
            260                 265                 270

Cys Asp Glu Cys Val Pro Tyr Pro Gly Cys Val His Gly Ser Cys Val
        275                 280                 285

Glu Pro Trp Gln Cys Asn Cys Glu Thr Asn Trp Gly Gly Leu Leu Cys
```

-continued

```
            290                 295                 300
Asp Lys Asp Leu Asn Tyr Cys Gly Ser His His Pro Cys Thr Asn Gly
305                 310                 315                 320

Gly Thr Cys Ile Asn Ala Glu Pro Asp Gln Tyr Arg Cys Thr Cys Pro
                325                 330                 335

Asp Gly Tyr Ser Gly Arg Asn Cys Glu Lys Ala Glu His Ala Cys Thr
                340                 345                 350

Ser Asn Pro Cys Ala Asn Gly Gly Ser Cys His Glu Val Pro Ser Gly
            355                 360                 365

Phe Glu Cys His Cys Pro Ser Gly Trp Ser Gly Pro Thr Cys Ala Leu
370                 375                 380

Asp Ile Asp Glu Cys Ala Ser Asn Pro Cys Ala Ala Gly Gly Thr Cys
385                 390                 395                 400

Val Asp Gln Val Asp Gly Phe Glu Cys Ile Cys Pro Glu Gln Trp Val
                405                 410                 415

Gly Ala Thr Cys Gln Leu Asp Ala Asn Glu Cys Glu Gly Lys Pro Cys
                420                 425                 430

Leu Asn Ala Phe Ser Cys Lys Asn Leu Ile Gly Gly Tyr Tyr Cys Asp
            435                 440                 445

Cys Ile Pro Gly Trp Lys Gly Ile Asn Cys His Ile Asn Val Asn Asp
450                 455                 460

Cys Arg Gly Gln Cys Gln His Gly Gly Thr Cys Lys Asp Leu Val Asn
465                 470                 475                 480

Gly Tyr Gln Cys Val Cys Pro Arg Gly Phe Gly Gly Arg His Cys Glu
                485                 490                 495

Leu Glu Arg Asp Lys Cys Ala Ser Ser Pro Cys His Ser Gly Gly Leu
                500                 505                 510

Cys Glu Asp Leu Ala Asp Gly Phe His Cys His Cys Pro Gln Gly Phe
            515                 520                 525

Ser Gly Pro Leu Cys Glu Val Asp Val Asp Leu Cys Glu Pro Ser Pro
            530                 535                 540

Cys Arg Asn Gly Ala Arg Cys Tyr Asn Leu Glu Gly Asp Tyr Tyr Cys
545                 550                 555                 560

Ala Cys Pro Asp Asp Phe Gly Gly Lys Asn Cys Ser Val Pro Arg Glu
                565                 570                 575

Pro Cys Pro Gly Gly Ala Cys Arg Val Ile Asp Gly Cys Gly Ser Asp
                580                 585                 590

Ala Gly Pro Gly Met Pro Gly Thr Ala Ala Ser Gly Val Cys Gly Pro
            595                 600                 605

His Gly Arg Cys Val Ser Gln Pro Gly Gly Asn Phe Ser Cys Ile Cys
610                 615                 620

Asp Ser Gly Phe Thr Gly Thr Tyr Cys His Glu Asn Ile Asp Asp Cys
625                 630                 635                 640

Leu Gly Gln Pro Cys Arg Asn Gly Gly Thr Cys Ile Asp Glu Val Asp
                645                 650                 655

Ala Phe Arg Cys Phe Cys Pro Ser Gly Trp Glu Gly Glu Leu Cys Asp
                660                 665                 670

Thr Asn Pro Asn Asp Cys Leu Pro Asp Pro Cys His Ser Arg Gly Arg
            675                 680                 685

Cys Tyr Asp Leu Val Asn Asp Phe Tyr Cys Ala Cys Asp Asp Gly Trp
690                 695                 700

Lys Gly Lys Thr Cys His Ser Arg Glu Phe Gln Cys Asp Ala Tyr Thr
705                 710                 715                 720
```

```
Cys Ser Asn Gly Gly Thr Cys Tyr Asp Ser Gly Asp Thr Phe Arg Cys
                725                 730                 735

Ala Cys Pro Pro Gly Trp Lys Gly Ser Thr Cys Ala Val Ala Lys Asn
            740                 745                 750

Ser Ser Cys Leu Pro Asn Pro Cys Val Asn Gly Gly Thr Cys Val Gly
            755                 760                 765

Ser Gly Ala Ser Phe Ser Cys Ile Cys Arg Asp Gly Trp Glu Gly Arg
        770                 775                 780

Thr Cys Thr His Asn Thr Asn Asp Cys Asn Pro Leu Pro Cys Tyr Asn
785                 790                 795                 800

Gly Gly Ile Cys Val Asp Gly Val Asn Trp Phe Arg Cys Glu Cys Ala
            805                 810                 815

Pro Gly Phe Ala Gly Pro Asp Cys Arg Ile Asn Ile Asp Glu Cys Gln
            820                 825                 830

Ser Ser Pro Cys Ala Tyr Gly Ala Thr Cys Val Asp Glu Ile Asn Gly
            835                 840                 845

Tyr Arg Cys Ser Cys Pro Pro Gly Arg Ala Gly Pro Arg Cys Gln Glu
        850                 855                 860

Val Ile Gly Phe Gly Arg Ser Cys Trp Ser Arg Gly Thr Pro Phe Pro
865                 870                 875                 880

His Gly Ser Ser Trp Val Glu Asp Cys Asn Ser Cys Arg Cys Leu Asp
            885                 890                 895

Gly Arg Arg Asp Cys Ser Lys Val Trp Cys Gly Trp Lys Pro Cys Leu
        900                 905                 910

Leu Ala Gly Gln Pro Glu Ala Leu Ser Ala Gln Cys Pro Leu Gly Gln
        915                 920                 925

Arg Cys Leu Glu Lys Ala Pro Gly Gln Cys Leu Arg Pro Pro Cys Glu
        930                 935                 940

Ala Trp Gly Glu Cys Gly Ala Glu Glu Pro Ser Thr Pro Cys Leu
945                 950                 955                 960

Pro Arg Ser Gly His Leu Asp Asn Asn Cys Ala Arg Leu Thr Leu His
            965                 970                 975

Phe Asn Arg Asp His Val Pro Gln Gly Thr Thr Val Gly Ala Ile Cys
            980                 985                 990

Ser Gly Ile Arg Ser Leu Pro Ala  Thr Arg Ala Val Ala  Arg Asp Arg
            995                 1000                1005

Leu Leu  Val Leu Leu Cys Asp  Arg Ala Ser Ser Gly  Ala Ser Ala
    1010                1015                1020

Val Glu  Val Ala Val Ser Phe  Ser Pro Ala Arg Asp  Leu Pro Asp
    1025                1030                1035

Ser Ser  Leu Ile Gln Gly Ala  Ala His Ala Ile Val  Ala Ala Ile
    1040                1045                1050

Thr Gln  Arg Gly Asn Ser Ser  Leu Leu Leu Ala Val  Thr Glu
    1055                1060                1065

<210> SEQ ID NO 6
<211> LENGTH: 45
<212> TYPE: PRT
<213> ORGANISM: Artificial Sequence
<220> FEATURE:
<223> OTHER INFORMATION: Peptide from homo sapiens

<400> SEQUENCE: 6

Val Arg Cys Asp Glu Asn Tyr Tyr Ser Ala Thr Cys Asn Lys Phe Cys
1               5                   10                  15
```

```
Arg Pro Arg Asn Asp Phe Phe Gly His Tyr Thr Cys Asp Gln Tyr Gly
            20                  25                  30

Asn Lys Ala Cys Met Asp Gly Trp Met Gly Lys Glu Cys
        35                  40                  45

<210> SEQ ID NO 7
<211> LENGTH: 542
<212> TYPE: PRT
<213> ORGANISM: Homo sapiens

<400> SEQUENCE: 7

Met Gly Ser Arg Cys Ala Leu Ala Leu Ala Val Leu Ser Ala Leu Leu
1               5                   10                  15

Cys Gln Val Trp Ser Ser Gly Val Phe Glu Leu Lys Leu Gln Glu Phe
            20                  25                  30

Val Asn Lys Lys Gly Leu Leu Gly Asn Arg Asn Cys Cys Arg Gly Gly
        35                  40                  45

Ala Gly Pro Pro Pro Cys Ala Cys Arg Thr Phe Phe Arg Val Cys Leu
    50                  55                  60

Lys His Tyr Gln Ala Ser Val Ser Pro Glu Pro Pro Cys Thr Tyr Gly
65                  70                  75                  80

Ser Ala Val Thr Pro Val Leu Gly Val Asp Ser Phe Ser Leu Pro Asp
                85                  90                  95

Gly Gly Gly Ala Asp Ser Ala Phe Ser Asn Pro Ile Arg Phe Pro Phe
            100                 105                 110

Gly Phe Thr Trp Pro Gly Thr Phe Ser Leu Ile Ile Glu Ala Leu His
        115                 120                 125

Thr Asp Ser Pro Asp Asp Leu Ala Thr Glu Asn Pro Glu Arg Leu Ile
    130                 135                 140

Ser Arg Leu Ala Thr Gln Arg His Leu Thr Val Gly Glu Glu Trp Ser
145                 150                 155                 160

Gln Asp Leu His Ser Ser Gly Arg Thr Asp Leu Lys Tyr Ser Tyr Arg
                165                 170                 175

Phe Val Cys Asp Glu His Tyr Tyr Gly Glu Gly Cys Ser Val Phe Cys
            180                 185                 190

Arg Pro Arg Asp Asp Ala Phe Gly His Phe Thr Cys Gly Glu Arg Gly
        195                 200                 205

Glu Lys Val Cys Asn Pro Gly Trp Lys Gly Pro Tyr Cys Thr Glu Pro
    210                 215                 220

Ile Cys Leu Pro Gly Cys Asp Glu Gln His Gly Phe Cys Asp Lys Pro
225                 230                 235                 240

Gly Glu Cys Lys Cys Arg Val Gly Trp Gln Gly Arg Tyr Cys Asp Glu
                245                 250                 255

Cys Ile Arg Tyr Pro Gly Cys Leu His Gly Thr Cys Gln Gln Pro Trp
            260                 265                 270

Gln Cys Asn Cys Gln Glu Gly Trp Gly Gly Leu Phe Cys Asn Gln Asp
        275                 280                 285

Leu Asn Tyr Cys Thr His His Lys Pro Cys Lys Asn Gly Ala Thr Cys
    290                 295                 300

Thr Asn Thr Gly Gln Gly Ser Tyr Thr Cys Ser Cys Arg Pro Gly Tyr
305                 310                 315                 320

Thr Gly Ala Thr Cys Glu Leu Gly Ile Asp Glu Cys Asp Pro Ser Pro
                325                 330                 335

Cys Lys Asn Gly Gly Ser Cys Thr Asp Leu Glu Asn Ser Tyr Ser Cys
```

-continued

```
                  340                 345                 350
Thr Cys Pro Pro Gly Phe Tyr Gly Lys Ile Cys Glu Leu Ser Ala Met
        355                 360                 365
Thr Cys Ala Asp Gly Pro Cys Phe Asn Gly Arg Cys Ser Asp Ser
    370                 375                 380
Pro Asp Gly Gly Tyr Ser Cys Arg Cys Pro Val Gly Tyr Ser Gly Phe
385                 390                 395                 400
Asn Cys Glu Lys Lys Ile Asp Tyr Cys Ser Ser Pro Cys Ser Asn
                405                 410                 415
Gly Ala Lys Cys Val Asp Leu Gly Asp Ala Tyr Leu Cys Arg Cys Gln
                420                 425                 430
Ala Gly Phe Ser Gly Arg His Cys Asp Asn Val Asp Asp Cys Ala
            435                 440                 445
Ser Ser Pro Cys Ala Asn Gly Gly Thr Cys Arg Asp Gly Val Asn Asp
    450                 455                 460
Phe Ser Cys Thr Cys Pro Pro Gly Tyr Thr Gly Arg Asn Cys Ser Ala
465                 470                 475                 480
Pro Val Ser Arg Cys Glu His Ala Pro Cys His Asn Gly Ala Thr Cys
                485                 490                 495
His Gln Arg Gly His Gly Tyr Val Cys Glu Cys Ala Arg Ser Tyr Gly
                500                 505                 510
Gly Pro Asn Cys Gln Phe Leu Leu Pro Glu Leu Pro Pro Gly Pro Ala
            515                 520                 525
Val Val Asp Leu Thr Glu Lys Leu Glu Gly Gln Gly Gly Pro
    530                 535                 540

<210> SEQ ID NO 8
<211> LENGTH: 45
<212> TYPE: PRT
<213> ORGANISM: Artificial Sequence
<220> FEATURE:
<223> OTHER INFORMATION: Peptide from homo sapiens

<400> SEQUENCE: 8

Phe Val Cys Asp Glu His Tyr Tyr Gly Glu Gly Cys Ser Val Phe Cys
1               5                   10                  15
Arg Pro Arg Asp Asp Ala Phe Gly His Phe Thr Cys Gly Glu Arg Gly
                20                  25                  30
Glu Lys Val Cys Asn Pro Gly Trp Lys Gly Pro Tyr Cys
            35                  40                  45

<210> SEQ ID NO 9
<211> LENGTH: 45
<212> TYPE: PRT
<213> ORGANISM: Artificial Sequence
<220> FEATURE:
<223> OTHER INFORMATION: Peptide from consensus between Rattus
      norvegicus and homo sapiens
<220> FEATURE:
<221> NAME/KEY: MISC_FEATURE
<222> LOCATION: (1)..(2)
<223> OTHER INFORMATION: Xaa = any amino acid
<220> FEATURE:
<221> NAME/KEY: MISC_FEATURE
<222> LOCATION: (5)..(6)
<223> OTHER INFORMATION: Xaa = any amino acid
<220> FEATURE:
<221> NAME/KEY: MISC_FEATURE
<222> LOCATION: (9)..(11)
<223> OTHER INFORMATION: Xaa = any amino acid
<220> FEATURE:
<221> NAME/KEY: MISC_FEATURE
```

```
<222> LOCATION: (13)..(14)
<223> OTHER INFORMATION: Xaa = any amino acid
<220> FEATURE:
<221> NAME/KEY: MISC_FEATURE
<222> LOCATION: (20)..(20)
<223> OTHER INFORMATION: Xaa = any amino acid
<220> FEATURE:
<221> NAME/KEY: MISC_FEATURE
<222> LOCATION: (22)..(22)
<223> OTHER INFORMATION: Xaa = any amino acid
<220> FEATURE:
<221> NAME/KEY: MISC_FEATURE
<222> LOCATION: (26)..(27)
<223> OTHER INFORMATION: Xaa = any amino acid
<220> FEATURE:
<221> NAME/KEY: MISC_FEATURE
<222> LOCATION: (29)..(31)
<223> OTHER INFORMATION: Xaa = any amino acid
<220> FEATURE:
<221> NAME/KEY: MISC_FEATURE
<222> LOCATION: (33)..(33)
<223> OTHER INFORMATION: Xaa = any amino acid
<220> FEATURE:
<221> NAME/KEY: MISC_FEATURE
<222> LOCATION: (35)..(35)
<223> OTHER INFORMATION: Xaa = any amino acid
<220> FEATURE:
<221> NAME/KEY: MISC_FEATURE
<222> LOCATION: (37)..(38)
<223> OTHER INFORMATION: Xaa = any amino acid
<220> FEATURE:
<221> NAME/KEY: MISC_FEATURE
<222> LOCATION: (41)..(41)
<223> OTHER INFORMATION: Xaa = any amino acid
<220> FEATURE:
<221> NAME/KEY: MISC_FEATURE
<222> LOCATION: (43)..(44)
<223> OTHER INFORMATION: Xaa = any amino acid

<400> SEQUENCE: 9

Xaa Xaa Cys Asp Xaa Xaa Tyr Tyr Xaa Xaa Xaa Cys Xaa Xaa Phe Cys
1               5                   10                  15

Arg Pro Arg Xaa Asp Xaa Phe Gly His Xaa Xaa Cys Xaa Xaa Xaa Gly
            20                  25                  30

Xaa Lys Xaa Cys Xaa Xaa Gly Trp Xaa Gly Xaa Xaa Cys
        35                  40                  45
```

DEVICES FOR PROMOTING EPITHELIAL CELL DIFFERENTIATION AND KERATINIZATION

STATEMENT OF GOVERNMENT LICENSE RIGHTS

This invention was made with government support under grant number EEC-9529161 awarded by National Science Foundation. The government has certain rights in the invention.

FIELD OF THE INVENTION

The present invention relates to methods and compositions for promoting epithelial cell differentiation.

BACKGROUND OF THE INVENTION

Control of epithelial cell differentiation has important applications in tissue engineering, wound healing and medical devices, such as percutaneous devices. Epithelial tissues such as skin and mucosal tissue typically contain a nonviable barrier layer. Such layers provide various essential functions to a mammal, including the retention of water, exclusion of hostile elements of the environment, such as toxins, allergens or pathogens. All external surfaces of the body are lined by epithelial cells, which provide an important barrier function. In the skin, mouth, and esophagus, this barrier is provided by stratified squamous epithelial cells (see Leeson, T. S., and Leeson, C. R., *Histology: 4th Ed.* Philadelphia, W. B. Sauders (1981)). In these stratified structures, the basal layer contains the stem or progenitor cells. Once these stem cells or progenitor cells are stimulated to enter the differentiation pathway, their protein expression changes and they move toward the surface, eventually to be sloughed off. (Eckert, R. L. et al., *Physiol Rev.* 77(2):397-424 (1997)). This process provides a constant renewal of the epithelial barrier. For example, the barrier of the skin, stratum corneum, is formed of non-viable anucleate keratinocytes that have undergone a differentiation and apoptotic events to become corneocytes.

In the context of tissue engineering, many organs and tissues require the development of a competent epithelial lining, including, but not limited to skin, esophagus and oral mucosa, however, the molecular events underlying the growth-arrest, terminal differentiation and apoptosis of the keratinocytes and corneogenesis remain elusive (see, e.g., Roop, *Science* 267:474-75 (1995)). Currently, the most widely studied inducer of keratinocyte differentiation is the calcium ion. (Menon et al., *Cell. Tissue Res.* 270:503-512 (1992)).

The Notch signaling pathway is important in regulating development, such as cell growth, proliferation, survival, migration and differentiation. Notch is a type I transmembrane receptor that is activated when bound by a transmembrane Notch ligand containing a Delta, Serrate, Lag-s ("DSL") conserved domain expressed on the surface of an adjacent cell. Currently there are four known mammalian Notch receptors (Notch 1-4) and four mammalian Notch ligands containing a DSL domain (Delta 1, 2 and Jagged 1, 2) (Artavanis-Tsakonas et al., *Science* 268:225-232 (1995)). The DSL family of Notch ligands all have multiple epidermal growth factor (EGF) regions in their extracellular domains and they all possess a characteristic DSL domain which is required for function. Henderson et al., *Development* 120: 2913-2924 (1994)). The Notch signaling pathway is initiated through direct cell-cell interactions between the Notch receptors and Notch DSL containing ligands. Upon binding of Notch by its ligand, the transmembrane domain of Notch is proteolytically cleaved and translocates to the nucleus where it binds CSL, the universal transcriptional effector of Notch signaling, thereby inducing gene transcription (see Schweisguth, F., *Curr. Biol.* 14(3):R129-138 (2004)). In addition, there is evidence that other CSL-independent modes of Notch signaling exist and research is ongoing in this area (see Martinez Arias et al., *Curr. Opin. Gen. Dev.* 12:524-533 (2002)).

Since both the Notch ligand and Notch receptor are transmembrane proteins, it is generally believed that direct cell-cell interactions are required for activating the Notch signaling pathway. Notch signaling is implicated in many developmental processes in a variety of cell types. It has been shown that Jagged-Notch signaling specifies cell fate, regulates pattern formation, defines boundaries between different cell types, and modulates cell development of the vasculature (see Shimizu, K. et al., *J. Biol. Chem.* 274:32961 (1999)). It has further been shown that soluble, non-transmembrane forms of Jagged 1 are capable of maintaining the survival and enhance the expansion of human stem cells that are capable of reconstituting hematopoietic lineages in vivo (see Karanu, F. et al., *J. Exp. Med* 192:1365 (2000)). However, depending on the cell types involved and how the soluble forms of the Notch ligand are presented, Notch ligand binding can result in either activation or inhibition of Notch signaling. (See Hicks C. et al., *J. Neurosci. Res.* 68:655 (2002)).

Research has been previously performed to evaluate the effect of Notch signaling on stratified squamous epithelial cells, however, previous studies have presented Notch ligands as either soluble proteins or expressed on the surface of adjacent cells. Depending on how soluble forms of the Notch ligand are presented, ligand binding can result in activation or inhibition of Notch signaling (Hicks et al., *J. Neurosci. Res.* 68:655 (2002)).

SUMMARY OF THE INVENTION

In accordance with the foregoing, in one aspect, the present invention provides a biomaterial having at least one biocompatible surface. The biocompatible surface comprises a plurality of immobilized Notch ligand molecules, wherein the plurality of immobilized Notch ligand molecules are capable of promoting differentiation in one or more epithelial cells. In some embodiments, the Notch ligand molecules comprise a DSL domain having the amino acid sequence set forth in SEQ ID NO:9. The biomaterials of the invention are useful in any situation where promotion of epithelial cell differentiation is desired, including for example, in vivo applications in a mammalian subject, or in vitro applications in the context of tissue engineering.

In another aspect, the present invention provides an implantable medical device comprising a layer of a biomaterial. The biomaterial has at least one biocompatible surface comprising a plurality of immobilized Notch ligand molecules, wherein the plurality of Notch ligand molecules are capable of promoting differentiation in one or more epithelial cells. As described more fully herein, the implantable medical devices of the invention are useful in any situation where promotion of epithelial differentiation is desired, such as promotion of epithelial cell differentiation in the tissue surrounding a catheter to form a protective keratin barrier.

Another aspect of the invention provides methods for promoting epithelial cell differentiation. The methods of this aspect of the invention include the step of contacting one or more epithelial cells with a biomaterial comprising an amount of immobilized Notch ligand molecules sufficient to promote differentiation in the one or more epithelial cells.

The methods of this aspect of the invention can be practiced in vivo or in vitro. Examples of contacting one or more epithelial cells with the biomaterial in accordance with this aspect of the invention include applications in wound healing, modulating epithelial differentiation in tissue surrounding biomaterials and tissue engineering, as described in more detail herein.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1B shows an alignment of amino acid sequences within the DSL domain of the mammalian Notch ligands shown in FIG. 1A, in accordance with an embodiment of the present invention;

FIG. 7 shows a perspective view of a representative medical device of the invention with a portion of the surface layer removed to expose the underlying device body, in accordance with an embodiment of the present invention;

FIG. 8 shows a transverse cross-section of the medical device of FIG. 7; and

FIG. 9 shows the immobilized Notch ligand bound to the surface layer of the medical device, in accordance with an embodiment of the present invention.

DETAILED DESCRIPTION OF THE PREFERRED EMBODIMENT

Figure 1A:
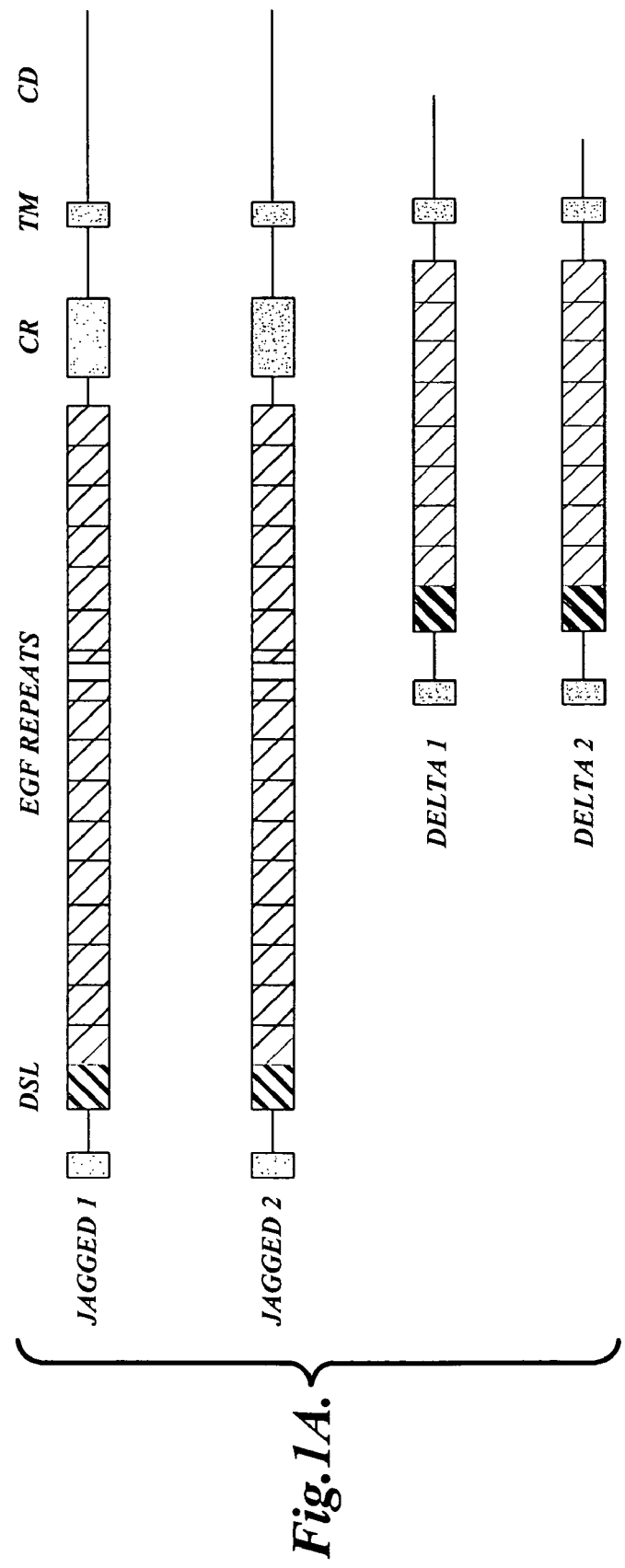
FIG. 1A illustrates the domain structure of several mammalian Notch ligands in accordance with an embodiment of the present invention.

Unless specifically defined herein, all terms used herein have the same meaning as they would to one skilled in the art of the present invention. Practitioners are particularly directed to Sambrook et al., *Molecular Cloning: A Laboratory Manual*, $2^{nd}$ *Ed.*, Cold Spring Harbor Press, Plainsview, N.Y. (1989), for definitions and terms of the art. Unless stated otherwise, all publications and patents that are cited in the present patent application are incorporated herein by reference in their entirety.

As used herein, the term "promoting epithelial cell differentiation" refers to stimuli which upon exposure to epithelial cells results in a differentiated epithelial cell phenotype in a portion of the exposed cells.

As used herein, the term "differentiated epithelial cell" refers to epithelial cells that have increased expression of one or more of the following art-recognized differentiation markers: involucrin, loricrin, filaggrin and cytokeratin 10, as described in *Crit. Rev. Oral Biol. Med.* 11:383-408. Another mark of epithelial cell differentiation is the formation of tight junctions and barrier structures such as stratum corneum.

As used herein, the term "Notch ligand" refers to an art-recognized class of proteins (and their functional sequence variants that are members of the Notch ligand family, including Jagged, Lunatic-Fringe, Manic-Fringe, Radical-Fringe, Delta and Serrate, that bind to a Notch receptor. Notch ligands and the Notch signaling pathway are reviewed by J. S. Mumm and R. Kopan, *Developmental Biology* 228: 151-165 (2000).

As used herein, the term "biomaterial" refers to a nonviable material (synthetic and/or natural) that is to be used in contact with a physiological environment either in vivo or in vitro.

As used herein, the term "immobilized" means the covalent or noncovalent attachment of a Notch ligand to a surface of a biomaterial.

As used herein, the term "percent identity" or "percent identical", when used in connection with Notch ligand molecules useful in the practice of the present invention, is defined as the percentage of amino acid residues in a Notch ligand molecule sequence that are identical with the amino acid sequence of a specified Notch ligand molecule (such as the amino acid sequence of SEQ ID NO: 1), after aligning the Notch ligand sequences to achieve the maximum percent identity. When making the comparison, no gaps are introduced into the Notch ligand sequences in order achieve the best alignment.

Amino acid sequence identity can be determined, for example, in the following manner. The amino acid sequence of a Notch ligand (e.g., the amino acid sequence set forth in SEQ ID NO:1) is used to search a protein sequence database, such as the GenBank database using the BLASTP program. The program is used in the ungapped mode. Default filtering is used to remove sequence homologies due to regions of low complexity. The default parameters of BLASTP are utilized.

As used herein, the term "derivatives" of a Notch ligand protein or peptide fragment include an insertion, deletion, or substitution mutant. Preferably, any substitution mutation is conservative in that it minimally disrupts the biochemical properties of Notch signaling. Thus, where mutations are introduced to substitute amino acid residues, positively-charged residues (H, K and R) preferably are substituted with positively-charged residues; negatively-charged residues (D and E) are preferably substituted with negatively-charged residues; neutral polar residues (C, G, N, Q, S, T, and Y) are preferably substituted with neutral polar residues; and neutral non-polar residues (A, F, I, L, M, P, V, and W) are preferably substituted with neutral non-polar residues.

As used herein, the term "implantable medical device" refers to medical devices that are adapted to be implanted into the body of a mammal, including a human, during the normal operation of the device. The devices may be completely or partially implanted into the body of a mammal.

As used herein, the term "wound healing" includes healing of any injury or lesion in the skin, tissue, vasculature or nervous system of a mammalian subject and includes cell migration and differentiation of cells comprising the mesoderm, endoderm, ectoderm and/or neuroderm. The wound or injury may be the result of surgery, trauma, burn, and/or disease or condition.

In one aspect, the present invention provides a biomaterial having at least one biocompatible surface comprising a plurality of immobilized Notch ligand molecules capable of promoting differentiation in one or more epithelial cells.

Any Notch ligand molecule, such as a polypeptide or peptide fragment that binds to a Notch receptor and stimulates epithelial cell differentiation may be immobilized to a surface of a biomaterial in accordance with this aspect of the invention. Notch ligands are known in the art, examples of which include the Notch ligands encoded by the vertebrate genes Delta-1, Delta-2 and Jagged-1, Jagged-2 that have been isolated from humans, rats, mice, and chickens. (See Weinmaster, G., *Mol and Cell Neuroscience* 9:91-102 (1997).

Notch ligands are transmembrane domains and have a common domain structure. FIG. 1A illustrates the domain structure of representative vertebrate Notch ligands Jagged-1, Jagged-2, Delta-1 and Delta-2. As shown in FIG. 1A, each Notch ligand has an amino terminal end comprising a DSL (Delta, Serrate, Lag-2) consensus sequence located within the first 250 amino acids (counted from the amino-terminus of the mature protein), a series of repeated epidermal growth factor (EGF) domains, a transmembrane domain (TM) and cytoplasmic (CD) domain. As further shown in FIG. 1A, the Jagged-1 proteins are larger than the Delta proteins and contain twice the number of EGF domains as well as a cysteine-rich (CR) region. The DSL motif has been shown to be necessary for ligand binding to Notch receptors (see Shimizu, K et al., *J. Biol. Chem* 274:32961 (1999)).

The following representative Notch ligand molecules and portions thereof are useful in the practice of the invention. The amino acid sequence of the extracellular domain of rat Jagged-1 is provided herein as SEQ ID NO:1, which includes the rat Jagged-1 DSL sequence motif (SEQ ID NO:2). The amino acid sequence of the extracellular domain of human Jagged-1 is provided herein as SEQ ID NO:3, which includes the human Jagged-1 DSL sequence motif (SEQ ID NO:4). The amino acid sequence of the extracellular domain of human Jagged-2 is provided herein as SEQ ID NO:5, which includes the human Jagged-2 DSL sequence motif (SEQ ID NO:6). The amino acid sequence of the extracellular domain of human Delta-1 is provided herein as SEQ ID NO:7, which includes the human Delta-1 DSL sequence motif (SEQ ID NO:8). Other representative examples of useful Notch ligand molecules include Notch ligand molecules that are at least 70% identical (such as at least 80% identical, or such as at least 90% identical, or such as at least 95% identical) to the Notch ligand molecules consisting of the amino acid sequences set forth in SEQ ID NO:1; SEQ ID NO:3, SEQ ID NO:5, or SEQ ID NO:7.

FIG. 1B shows an alignment of each of the above-mentioned DSL sequence motifs contained within each of the Notch ligands shown in FIG. 1A. The shaded region in FIG. 1B shows amino acids that are conserved and are included in the consensus DSL sequence (SEQ ID NO:9). The left and right ends of the amino acid sequences in the sequence listing indicate amino terminal (hereinafter designated as N-terminal) and carboxyl terminal (hereinafter designated as C-terminal), respectively.

In accordance with one embodiment of this aspect of the invention, polypeptides comprising an extracellular domain of a Notch ligand including a DSL motif that mediates binding to a Notch receptor protein are immobilized to at least one surface of a biomaterial. In further embodiments, polypeptides comprising an extracellular domain of a Notch ligand comprising SEQ ID NO:9 are immobilized to at least one surface of a biomaterial. In additional embodiments, polypeptides comprising SEQ ID NO:2, SEQ ID NO: 4, SEQ ID NO:6 or SEQ ID NO:8 are immobilized to at least one surface of a biomaterial. In another embodiment, polypeptides comprising at least the N-terminal 250 amino acid region of SEQ ID NO:1, SEQ ID NO:3, SEQ ID NO:5, or SEQ ID NO:7 are immobilized to at least one surface of a biomaterial.

Notch ligand molecules and derivatives thereof useful in the present invention can be produced and recovered by any useful method and may be naturally isolated, chemically synthesized, or produced by recombinant techniques from a prokaryotic or eukaryotic host, including, for example, bacterial, yeast, insect, mammalian, avian and higher plant cells. For example, the Notch ligand molecules can be synthesized using standard direct peptide synthesizing techniques (Bodanszky, *Principles of Peptide Synthesis*, Springer-Verlag, Heidelberg: 1984), such as solid-phase synthesis (see, e.g. Merrifield, *J. Am. Chem. Soc.* 85:2149-54(1993)). Alternatively, a gene encoding the Notch ligand can be subcloned into an appropriate expression vector using well known molecular genetic techniques. The protein can then be produced by a host cell and isolated therefrom. Any appropriate expression vector (see, e.g., Pouwels et al., *Cloning Vectors: A Laboratory Manual* (Elsevier, N.Y., 1985)) and corresponding suitable host cells can be employed for production of Notch polypeptides. Expression hosts include, but are not limited to, bacterial species, mammalian or insect host cell systems including baculovirus systems (see, e.g., Luckow et al., *Bio/Technology* 6:47 (1988)), and established cell lines such as 293, COS-7, C127, 3T3, CHO, HeLa, BHK, etc. For example, Notch ligand molecules may be purified using ammonium sulfate or ethanol precipitation, gel filtration, hydrophobic interaction chromatography, affinity chromatography, hydroxylapatite chromatography, and high performance liquid chromatography. Art-recognized techniques for the purification of proteins and peptides are set forth, for example, in *Methods in Enzymology*, Vol. 182, Guide to Protein Purification, Murray P. Deutscher, ed (1990).

The biomaterial for use in this aspect of the invention may comprise any suitable biocompatible material such as a polymeric material, including synthetic polymers, naturally-occurring polymers, or mixtures thereof. Exemplary synthetic biocompatible polymers for forming the biocompatible material include, but are not limited to, 2-hydroxyethyl methacrylate (HEMA), silicone rubber, poly(ε-caprolactone), dimethylacrylate, polysulfone, (poly)methyl methacrylate (PMMA), soluble Teflon-AF, (poly) ethylenetetraphthalate (PET, Dacron), Nylon, polyvinyl alcohol, polyurethane, and mixtures thereof. Exemplary naturally-occurring biocompatible polymers useful for forming the biomaterial include, but are not limited to fibrous or globular proteins, complex carbohydrates, glycosaminoglycans, or mixtures thereof. Thus, the biomaterial may include collagens of all types, elastin, hyaluronic acid, alginic acid, desmin, versican, matricellular proteins such as SPARC (osteonectin), osteopontin, thrombospondin 1 and 2, fibrin, fibronectin, virtonectin, albumin, etc.

The biomaterial can be formed into any desired shape and includes at least one surface having a biocompatible material suitable for contact with a physiological environment compatible with epithelial cell growth. For example, biomaterials of the invention may be in the form of a gel such as a hydrogel, a sphere, microparticle(s), nanoparticle(s), an implantable structure, a tissue scaffold, suture materials, and the like as described in more detail below. The biocompatible surface may cover all of the biomaterial, or substantially all of the biomaterial, (such as from at least 80%, or at least 90% up to 99% of the biomaterial), or a portion of the biomaterial, such as less than 80% of the biomaterial.

In some embodiments, the biomaterial comprises a hydrogel, such as a biodegradable hydrogel with an outer surface to which Notch ligand molecules are immobilized. A hydrogel may be formed, for example, by reacting low-molecular-weight poly(ε-caprolactone) diol with an excess of methacryloyl chloride to give a polyester with methacrylate endgroups, and copolymerizing this compound with 2-hydroxyethyl methacrylate (HEMA) to yield a cross-linked hydrogel with hydrolyzable linkages.

In other embodiments, the biomaterial comprises a porous matrix having a plurality of surfaces to which Notch ligand molecules are immobilized. Porous matrices for use as a biomaterial include those prepared from tendon or dermal collagen, as may be obtained from a variety of commercial sources, (e.g., Sigma and Collagen Corporation), or collagen matrices prepared as described in U.S. Pat. Nos. 4,394,370 and 4,975,527. One useful collagenous material is termed UltraFiber™, and is obtainable from Norian Corp. (Mountain View, Calif.). In accordance with this embodiment, the Notch ligand molecule may include a C-terminal collagen binding domain that is immobilized to the collagen contained in the collagen matrix.

Certain types of polymeric matrices may also be used to form the biomaterial, such as acrylic ester polymers and lactic acid polymers, as disclosed, for example, in U.S. Pat. Nos. 4,526,909, and 4,563,489. Particular examples of useful polymers are those of orthoesters, anhydrides, propylene-cofumarates, or a polymer of one or more α-hydroxy carboxylic acid monomers, (e.g., α-hydroxy acetic acid (glycolic acid) and/or α-hydroxy propionic acid (lactic acid)).

In some embodiments, the biomaterial comprises porous biomaterials having a biocompatible polymer scaffold defining an array of pores. The pores preferably have a similar diameter, such as a mean diameter from about 20 to about 90 micrometers, wherein substantially all the pores are each connected to at least 4 other pores, and wherein the diameter of substantially all the connections between the pores is between about 15% and about 40% of the mean diameter of the pores, as described in pending PCT Patent App. No. PCT/US2004/032639, filed Oct. 1, 2004, and hereby incorporated by reference.

In another embodiment, the biomaterial is in the form of biodegradable microparticles, wherein the microparticles are particles having a diameter of preferably less than 1.0 mm, and more preferably between 1.0 and 100.0 microns. Microparticles include microspheres, which are typically solid spherical microparticles. Microparticles for use in the present invention can be made using a variety of biodegradable polymers including, for example, poly(hydroxy acids) including polylactic acid, polyglycolic acid, and copolymers thereof, polyanhydrides, polyorthoesters, and poly(lactic acid-co-glycolic acid), as described in U.S. Pat. No. 6,706,289, the disclosure of which is hereby incorporated by reference. A variety of techniques are known in the art for forming microparticles, including for example, single or double emulsion steps followed by solvent removal.

In another embodiment, the biomaterial is in the form of biodegradable nanoparticles, wherein the nanoparticles are particles having a diameter of preferably between about 20.0 nanometers and about 2.0 microns, more preferably between about 100 nanometers and about 1.0 micron. Nanoparticle mediated delivery systems are known in the art, (see e.g., Kip, J. E., *Int. J. Pharm.* 284(1-2): 109-122 (2004); Moghimi S. M. et al., *Trends Biotechnol.* 18(10): 412-420 (2000); Brannon-Peppas L. et al., and *Adv. Drug Deliv. Rev.* 56(11): 1649-1659 (2004)). Nanoparticles may be injected for systemic or localized delivery into a mammalian subject. Formation of nanoparticles may be achieved as described for microparticles, except that the speed of mixing or homogenization is used to reduce the size of the polymer to below about 2.0 microns. Suitable techniques for making nanoparticles are described in WO 97/04747, the disclosure of which is hereby incorporated by reference.

The plurality of Notch ligand molecules can be immobilized to at least one surface on the biomaterial with any suitable method, including covalent or noncovalent attachment, that allows for the differentiation of one or more epithelial cells upon contact with the biomaterial surface comprising the immobilized Notch ligand. The Notch ligand may be immobilized by linking any portion of the ligand molecule to the biomaterial surface while retaining the ability of the immobilized ligand to stimulate a Notch receptor. For example, any amino acid comprising a reactable side chain contained in the Notch ligand may be used to immobilize the ligand molecule to the biomaterial surface, including for example, Asp, Glu, Lys, Arg, Cys, His and Tyr. In a preferred embodiment, the C-terminus of each Notch ligand molecule is immobilized to a surface of the biomaterial, thereby allowing the N-terminus of the Notch ligand molecule comprising the DSL motif to be oriented away from the surface of the biomaterial so that it is capable of stimulating a Notch receptor on an epithelial cell.

Figure 3A:
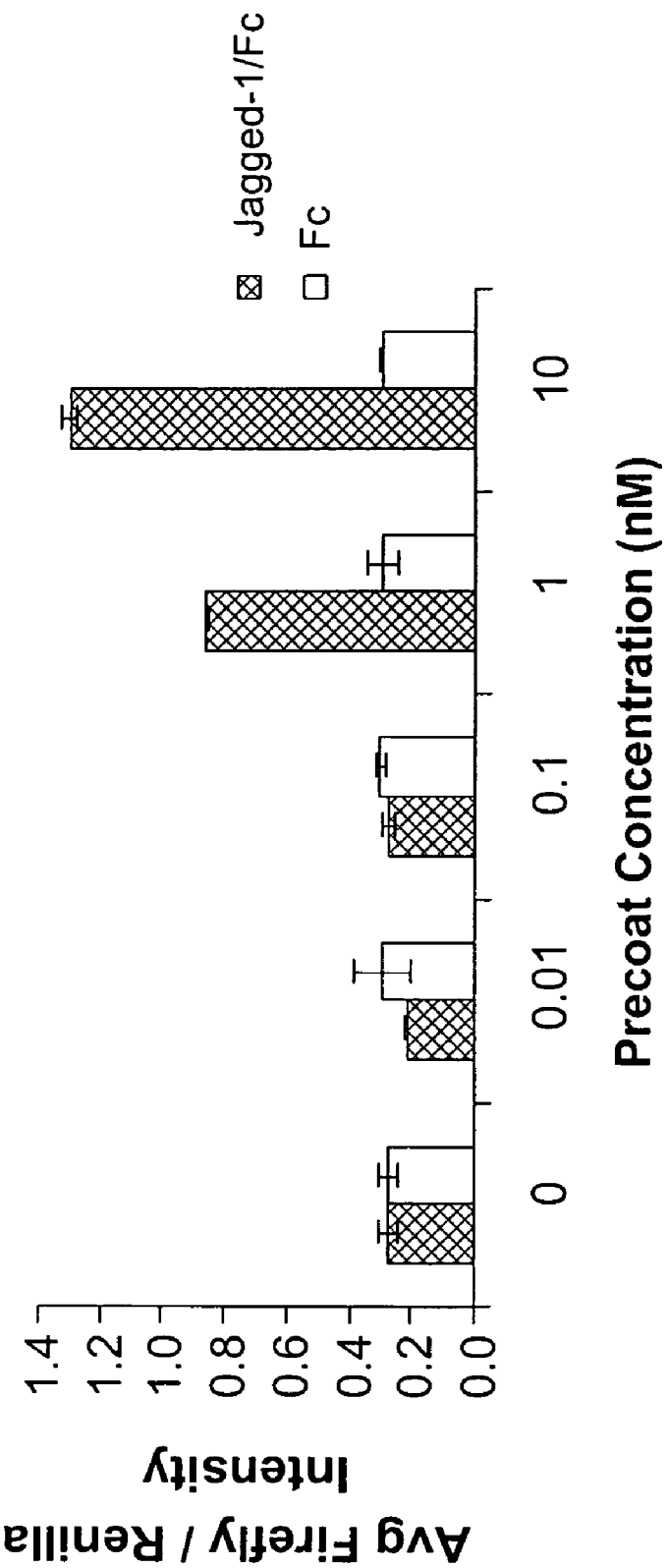
FIG. 3A graphically demonstrates that immobilized Notch ligand activates the Notch signaling pathway in esophageal epithelial cells, as described in Example 3, in accordance with an embodiment of the present invention.
Figure 3B:
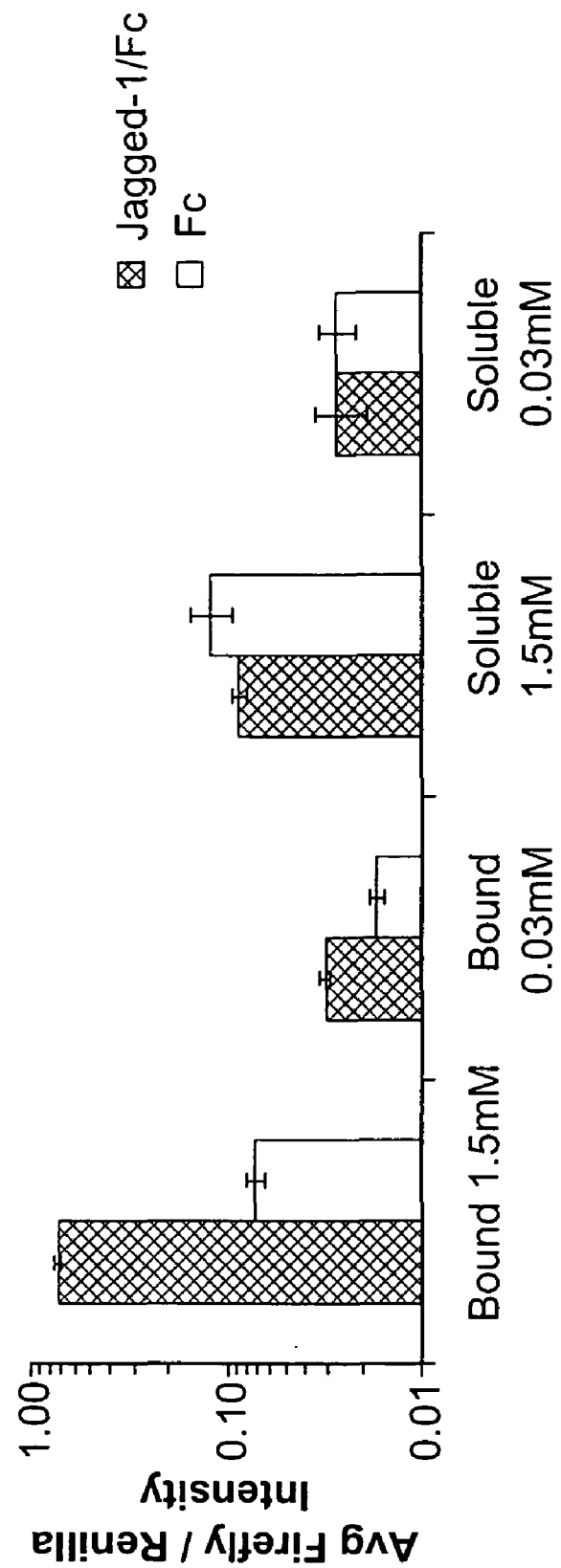
FIG. 3B graphically demonstrates that immobilized Notch ligand activates the Notch signaling pathway in esophageal epithelial cells with greater potency than soluble Notch ligand, as described in Example 3.

The present inventors have made the surprising discovery that immobilized Notch ligand is capable of stimulating the Notch signaling pathway and promoting epithelial cell differentiation as described in Examples 1-6 herein. The inventors have further shown the unexpected result that immobilized Notch ligand promotes epithelial cell differentiation much more effectively that soluble Notch ligand, as shown in FIGS. 3B and 4B, and described in Examples 3 and 4 herein. While not wishing to be bound by theory, the potent differentiation signal provided by the immobilized Notch ligand to epithelial cells may be due in part to the high local concentration of the Notch ligand provided at the interface between the biomaterial surface and the epithelial cell surface, and also may be due to proper Notch ligand presentation, similar to what naturally occurs during a cell-to-cell interaction.

In some embodiments, Notch ligand molecules are covalently attached to the surface of the biomaterial. Any functional group present on polymer molecules on the surface of the biomaterial can be used to covalently attach Notch ligand molecules to the biomaterial. In another embodiment, Notch ligand molecules, and/or fragments thereof that have the ability to promote epithelial cell differentiation are covalently attached to at least one surface of the biomaterial. Covalent attachment may be achieved by any of the following pairs of reactive groups (one member of the pair being present on a surface of the biomaterial, and the other member of the pair being present on the Notch ligand protein(s)): hydroxyl/carboxylic acid to yield an ester linkage; hydroxyl/anhydride to yield an ester linkage; hydroxyl/isocyanate to yield a urethane linkage, amine groups and the like. The following publications, incorporated herein by reference, describe additional examples of technologies that are useful for attaching biologically active molecules to polymer molecules, such as the biomaterial of the present invention: Nuttelman et al. (2001) *J. Biomed. Mater. Res.* 57:217-223; Rowley et al. (1999) *Biomaterials* 20:45-53; Hubbel (1995) *Biotechnology* 13:565-76; Massia & Hubbell (1990) *Anal. Biochem* 187: 292-301; Drumheller et al. (1994) *Anal. Biochem.* 222:380-8; Kobayashi & Ikada (1991) *Curr. Eye Res.* 10:899-908; Lin et al. (1992) *J. Biomaterial Sci. Polym. Ed.* 3:217-227; and Bellamkonda et al. (1995) *J. Biomed. Mater. Res.* 29:663-71.

In some embodiments, the Notch ligand molecule is a fusion protein comprising an N-terminal Notch-binding region including a DSL binding domain, such as SEQ ID NO: 2, SEQ ID NO:4, SEQ ID NO:6, SEQ ID NO:8 or SEQ ID NO:9 and a C-terminal binding region, wherein the C-terminal binding region binds either directly to a surface of the biomaterial, or binds to a binding agent disposed on a surface of the biomaterial. Examples of useful C-terminal binding regions include IgG Fc binding regions (see, for example, Askenazi et al., *Current Opin. Immun.* 9: 195-200 (1997), collagen binding regions (see, for example, Tuan et al., *Connect Tissue Res.* 34(1): 1-9 (1996), or myc epitopes (see, for example, Varnum-Finney et al., *Blood* 91:4084-4091 (1998)). For example, the Notch ligand molecule may have a C-terminal fusion with the Fc region of human $IgG_1$, which binds to Protein G disposed on one or more surfaces of the biomaterial, as described in Example 2.

In some embodiments, the Notch ligand molecule is immobilized to the biomaterial at concentrations of from about 0.01 nM to about 1 uM.

Epithelial cell differentiation may be assessed by any suitable method, many of which are known in the art (see e.g., *Crit. Rev. Oral Biol. Med.* 11:383-408 and *Phys Rev.* 77:397-424). Thus, for example, epithelial cell differentiation can be monitored by assaying for the production of certain markers, such as involucrin, loricrin, filaggrin and cytokeratin 10, as shown below in TABLE 1, described in EXAMPLE 4, and shown in FIG. 4. Another mark of epithelial cell differentiation is the formation of tight junctions and gross structures associated with differentiated epithelial cells, such as barrier structures, as described in EXAMPLE 5 and shown in FIG. 5 and FIG. 6. Formation of such a barrier structure can be assessed by histological examination of the tissue. For example, where the barrier is stratum corneum, its appearance in cutaneous epithelium will be readily apparent to one of skill in the art.

TABLE 1

Epithelial Differentiation Markers

| Protein | Function/Expression Profile |
|---------|------------------------------|
| Involucrin | Expressed in late spinous layers and granular layers<br>Major component of cornified envelope (CE)<br>Scaffolding protein involved in CD formation |
| Filaggrin | Expressed in granular layer<br>Aggregates Keratin intermediate filaments into tight bundles |
| Loricrin | Expressed in granular layer<br>Major CE component |
| Cytokeratin 10 | Cytoskeletal protein<br>Expressed in suprabasal layer |

The biomaterials of the invention are useful in any application in which epithelial cell differentiation is desired, including, but not limited to, tissue engineering and wound repair, as described in more detail below.

In another aspect, the present invention provides implantable medical devices comprising a substrate and a layer of a biomaterial, wherein the biomaterial comprises a biocompatible surface comprising a plurality of immobilized Notch ligand molecules capable of promoting differentiation in one or more epithelial cells. The implantable medical devices of the invention are adapted to be implanted into the body of a mammal, such as a human, during the normal operation of the device. Representative devices of the invention include, for example, catheters, bladder grafts, joint replacement hardware, bone replacement/substitute material, stents and biosensors.

FIG. 7 shows a representative implantable medical device 10 of the present invention. The device 10 includes a device body 12 to which is attached a layer of a biomaterial 14. In the embodiment shown in FIG. 7, biomaterial layer 14 has been partially removed to show device body 12 underneath. The device body 12 is indicated by hatching. FIG. 8 shows a cross-sectional view of medical device 12 shown in FIG. 7. As shown in FIG. 8, biomaterial layer 14 includes an internal surface 18 attached to device body 12 and an external surface 20. The biomaterial layer 14 may be formed as previously described herein.

FIG. 9 shows an exemplary embodiment of device 10 having biomaterial layer 14 that comprises a plurality of Notch ligand molecules 22. In the embodiment shown in FIG. 9, each Notch ligand molecule 22 includes an N-terminal Notch binding domain 24, including a DSL motif, forming external surface 20, attached via a linker region 26 to a C-terminal binding region 28 that binds to internal surface 18 of biomaterial layer 14.

As mentioned above, biomaterial 14 comprises immobilized molecules of Notch ligand molecules 22. The Notch ligand molecules 22 may be immobilized onto or within biomaterial layer 14 using any suitable means, such as, for example, covalent attachment or noncovalent attachment as described herein. The Notch ligand 22 may be any suitable type of Notch ligand as described herein. The amino terminal Notch binding region 24 includes a DSL binding region, such as, for example, a peptide region comprising SEQ ID NO:9. In some embodiments, the Notch ligand protein molecule further comprises a carboxy terminal fusion region, such as the Fc region of $IgG_1$ that is attached to Protein G disposed on the internal surface 18 of the biomaterial 14, as described in Example 2.

The biomaterial layer 14 can cover the whole of device body 12, substantially all of device body 12, (such as from at least 80%, or at least 90% up to 99% of the device body 12) or one or more parts of device body 12, such as an area of the device body 12 that is/will be in contact with living tissue in which it is desired to promote epithelial cell differentiation.

The medical devices 10 of the invention may be affixed to the surface of a living body, completely implanted into the soft tissue of an animal body (i.e., the entire device is implanted within the body), or the device may be partially implanted into an animal body (i.e., only part of the device is implanted within an animal body, the remainder of the device being located outside of the animal body). Representative examples of completely implantable medical devices 10 include, but are not limited to: vascular devices such as artificial vessels, natural and/or synthetic scaffolds that support tissue growth, drug delivery devices, prosthetic devices, ophthalmologic applications (contacts, corneal implants, intraocular lenses, etc), adhesives/sealants, shunts, bioelectrodes, dental devices/implants including periodontal bone substitute material for use in periodontal guided tissue regeneration, surgical staples/sutures, burn dressings, artificial skin grafts, transcutaneous devices, limb bioprostheses, and artificial organs.

Scaffolds may be either synthetic or naturally derived. Synthetic scaffolds may include, but are not limited to, polylactic acid, polyHema, polycaprolactone, polyurethanes, and polyesters. Examples of commercially available synthetic scaffolds that are suitable for use in the practice of the invention include, but are not limited to, open cell polylactic acid scaffold (BD Biosciences, Bedford, Mass.), Skelite™ tissue engineering scaffolds (Millenium Biologix Corp., Kingston, ON) and PGA Scaffolds (Synthecon Inc., Houston, Tex.). Examples of naturally derived scaffolds may include, but are not limited to, collagen, chitosan, polyhydroxybutyrate, and fibrin. Examples of commercially available natural scaffolds that are suitable for use in the practice of the invention include, but are not limited to, small intestine submucosa (Cook Biotech Inc., West Lafayette, Ind.), AlloDerm® (Lifecell, Branchburg, N.J.), collagen composite scaffolds (BD Biosciences, Bedford, Mass.) and calcium phosphate (BD Biosciences, Bedford, Mass.).

Representative examples of partially implantable medical devices include: biosensors (such as those used to monitor the level of drugs within a living body, or the level of glucose in a diabetic person) and percutaneous devices (such as catheters) that penetrate the skin and link a living body to a medical device, such as a kidney dialysis machine. The layer of biomaterial comprising Notch ligand molecules promotes epithelial cell differentiation and thereby improves the biocompatibility of the implanted medical devices, improves the sealing of skin to percutaneous devices (such as in-dwelling catheters or trans-cutaneous glucose sensors), thereby reducing the risk of infection associated with the use of such devices. Barrier formation is also improved.

Some medical devices 10 of the invention are adapted to be affixed to soft tissue of an animal, such as a mammal, including a human, during the normal course of operation of the medical device. These medical devices are typically affixed to the skin of a mammalian body. Examples of medical devices that are adapted to be affixed to soft tissue of an animal include skin substitutes, and wound or burn treatment devices (such as surgical bandages and transdermal patches).

The implantable or attachable device body 12 is a substrate that can be made from natural and/or synthetic material or combination of materials such as, for example, nitrocellulose, diazocellulose, glass, polystyrene, polyvinylchloride, polypropylene, polyethylene, dextran, Sepharose, agar, starch, nylon. Representative examples of synthetic polymers useful for making device body 12 include: (poly)urethane, (poly)carbonate, (poly)ethylene, (poly)propylene, (poly)lactic acid, (poly)galactic acid, (poly)acrylamide, (poly)methyl methacrylate and (poly)styrene. Useful natural polymers include collagen, hyaluronic acid and elastin. The surface of the device body 12 can be modified to include functional groups (e.g. carboxyl, amide, amino, ether, hydroxyl, cyano, nitrido, sulfanamido, acetylinic, epoxide, silanic, anhydric, succinimic, azido) for immobilizing a biomaterial thereto. Coupling chemistries include, but are not limited to, the formation of esters, ethers, amides, azido and sulfanamido derivatives, cyanate and other linkages to functional groups available of the biomaterial.

In some embodiments, a surface of a device body 12 that does not possess useful reactive groups can be treated with radio-frequency discharge plasma (RFGD) etching to generate reactive groups (e.g. treatment with oxygen plasma to introduce oxygen-containing groups; treatment with propyl amino plasma to introduce amine groups) in order to allow attachment of a biomaterial comprising Notch ligands, or active fragments thereof that have the ability to promote epithelial cell differentiation. When RFGD glow discharge plasma is created using an organic vapor, deposition of a polymeric overlayer occurs on the exposed surface. RFGD plasma deposited films offer several unique advantages. They are smooth, conformal, and uniform. Film thickness is easily controlled and ultrathin films (10-1000 Angstroms) are readily achieved, allowing for surface modification of a material without alteration to its bulk properties. Moreover, plasma films are highly-crosslinked and pin-hole free, and therefore chemically stable and mechanically durable. RFGD plasma deposition of organic thin films has been used in microelectronic fabrication, adhesion promotion, corrosion protection, permeation control, as well as biomaterials. (see, e.g., Ratner, U.S. Pat. No. 6,131,580).

In operation of medical device 10, due to the presence of immobilized Notch ligand molecules capable of promoting epithelial cell differentiation, as discussed above, biomaterial layer 14 promotes epithelial cell differentiation in the tissue surrounding device 10 within a mammalian subject, after implantation into, or attachment to tissue of a mammalian subject.

In another aspect, the present invention provides a method of promoting epithelial cell differentiation. The method includes the step of contacting one or more epithelial cells with a biomaterial comprising an amount of immobilized Notch ligand molecules sufficient to promote differentiation in the one or more epithelial cells.

The method of the invention may be practiced in connection with epithelial cells derived from, or found within, any type of epithelial tissue or in association with surrounding cell types (e.g., dermal cells, subdermal cells, melanocutes, glandular cells) such as skin, gut, intestine, bladder, urinary tracts, renal, esophagus, lung, tooth, cells of polarized structures (e.g., hair), and cutaneous tissue. Also included are all simple, pseudostratified and stratified epithelium including squamous, cuboidal, columnar and transitional epithelium. The method may be practiced on both non-keratinizing and keratinizing stratified squamous epithelial cells. In applications in which the method is applied to cutaneous tissue, the epithelial cell may be a keratinocyte or some other cell within cutaneous epithelial tissue. In applications in which the method is applied to extracutaneous epithelium, the epithelial cell may be within oral mucosa, cornea, gastrointestinal epithelia, urogenital epithelia, respiratory epithelia, etc.

The method of the invention may be applied in vivo to promote epithelial cell differentiation in any desired context.

For example, the method may be used to promote differentiation of epithelial cells within an epithelial tissue to form a barrier layer. In accordance with this embodiment of the method, a biomaterial comprising a surface having a plurality of immobilized Notch ligand molecules is contacted with epithelial cells within the epithelial tissue such that they are induced to form a barrier within the epithelium. For example, a barrier may be formed by contacting non-keratinizing stratified squamous epithelial cells with the biomaterial to form a barrier comprising a layer of cells having an increase in cell thickness. In another example, a barrier may be formed by contacting keratinizing stratified squamous epithelial cells with the biomaterial to form a barrier comprising a keratin layer. The biomaterial may be in any suitable form, such as an injectable biosphere, a hydrogel or the biomaterial may be attached to a medical device as described herein.

In one embodiment, the method includes the application of a biomaterial to a wound to promote wound healing. For example, in the practice of the method of this aspect of the invention, the biomaterial may be in the form of a hydrogel and contacted with epithelial cells within a wound site on or in a mammalian body. In wound healing, the formation of an epithelial lining is important to prevent infection and promote healing. (See *Biomaterials Science*, p. 602 (2004)). By using a biomaterial such as a hydrogel or other suitable form of biomaterial comprising immobilized Notch ligand to promote keratinization, a barrier may be rapidly formed in the wound healing environment, thereby excluding microbes while retaining water. In another example, the biomaterial may be in the form of a tissue sealer, such as a suture or staple and contacted with epithelial cells surrounding an incision in a mammalian body.

In another embodiment, the method includes the application of a biomaterial to a gingival epithelium to promote periodontal regeneration in the context of periodontal guided tissue regeneration. It has been shown that epithelial migration onto the root surface of a tooth inhibits periodontal regeneration. Application of a biomaterial comprising immobilized Notch ligand to the gingival epithelium adjacent to the site of regeneration, would promote growth arrest and differentiation of the epithelium rather than migration, in accordance with one embodiment of the method of the invention.

In additional in vivo applications, the method may be used as a treatment for any of a number of epithelial tissue disorders, such as disorders associated with dysfunctional epithelial barriers, abnormal barrier formation and/or function and the inability to differentiate properly (e.g. skin cancers). For example, the loss of integrity of the stratum corneum in skin can have any of a wide variety of medical consequences, such as increased risk of infection, excessive water loss, dermal irritation (e.g., dryness or itching), and other dermatological problems. Examples of such disorders include actinic keratosis, aged skin, alopecia (e.g., androgenic alopecia, alopecia greata, etc.), asteototic skin (dry skin, winter itch), Bowen's disease, cancers (e.g., keratocanthoma, squamous cell carcinoma, basal cell carcinoma, etc.), dermatitis (e.g., atopic dermatitis, allergic/irritant contact dermatitis, etc.), drug reactions, ichthyotic skin, photodamaged skin, psoriasis, sunburn, incontinentia pigmenti, tracheoesophageal disorders and the like. Similarly, other epithelial organ systems, such as oral mucosal, gastrointestinal tract, pulmonary system, etc., also are dependent on formation of an effective barrier to shield against noxious agents at the sites of interfacing between the host and environment. Altered cellular differentiation, such as a block in terminal differentiation, particularly in keratinocytes, can predispose a mammalian subject to the development of various skin cancers and other epithelial derived neoplasms at extracutaneous sites (see, e.g., Yuspa et al., *Cancer Res., Res.* 54:1178-89 (1994)).

In another embodiment, the method of the invention is applied in vivo to one or more epithelial cells in a living body surrounding a biomaterial layer attached to a medical device, such as a transcutaneous device (i.e. catheters, biosensors and the like). Infection of transcutaneous devices is a major medical problem. Because the catheter is not integrated into the epithelium, bacteria are able to migrate in the space between the catheter and the adjacent skin, thereby creating a haven for infection with opportunistic bacteria (see *Biomaterials Science*, p. 346 (2004); Schierholz J. M. et al, *J. Hosp. Infect.* 49(2):87-93 (2001)). By attaching a biomaterial to the catheter's surface, or directly modifying the catheter's surface to include immobilized Notch ligand, formation of a protective keratin barrier would be promoted.

In another embodiment, the biomaterial or surface of the device additionally includes an adhesive protein or peptide that promotes epithelial cell migration and/or attachment to the surface of a biomaterial, such as, for example, fibronectin, laminin, vitronectin, osteopontin, fibrinogen or collagen. For example, the adhesive protein is added to the biomaterial or surface of the device, such as a percutaneous device (e.g. catheter) comprising the immobilized Notch ligand. In accordance with this embodiment, the adhesive protein would attract epithelial cell attachment and/or migration to the surface of the biomaterial. Once the epithelial cells are contacted with the surface immobilized Notch ligand, in accordance with the methods of the invention, the Notch ligand would promote differentiation and keratinization of the epithelial cells, thus creating a competent barrier to prevent bacteria from migrating down the catheter to the patient.

In another embodiment, the method includes contacting the biomaterial with one or more epithelial cells in vitro. In accordance with such embodiments, a biomaterial having at least one surface comprising a plurality of immobilized Notch ligand molecules is contacted with epithelial cells in vitro such that they are induced to differentiate. The biomaterial may be provided as an in vitro cell culture substrate, such as an epithelial cell culture vessel or a scaffold structure in a tissue engineering system.

For example, in the context of tissue engineering, many organs and tissues require the development of a competent epithelial lining, including, but not limited to skin, esophagus and oral mucosa. (see *Principles of Tissue Engineering*, p. 879-890 (2000); *Ann Thorac. Surg.* 72:577-91; *J. Dent. Res* 79:798-805). By promoting differentiation of the epithelial cells using a biomaterial having a surface comprising an immobilized Notch ligand, the development of a stratified squamous epithelial lining in culture is accelerated. This provides several advantages including for example, shorter culture times required for tissue and/or organ growth and simplified culture conditions (i.e., no air-water interface). The resulting engineered tissue would have an intact epithelial lining with a competent keratin layer. An example of the use of the method of the invention to generate an esophageal construct, is provided in EXAMPLE 6.

In one such in vitro application, the invention provides a method for producing differentiated epidermis. In accordance with this embodiment of the method, at least one surface of a biomaterial comprising a plurality of immobilized Notch ligand molecules is placed in contact with undifferentiated, or partially differentiated epidermal tissue in an in vitro culture vessel for a time sufficient to promote differentiation of the epidermis into a mature epidermal structure, such as the presence of a barrier and/or substratum. The method may be used to culture epidermal tissue (e.g. skin or other epithelial grafts) for subsequent implantation into patients.

The following examples merely illustrate the best mode now contemplated for practicing the invention, but should not be construed to limit the invention.

EXAMPLE 1

This example demonstrates that Notch-1 and Jagged-1 proteins are expressed in normal human and rat esophageal tissue and cultured human and rat epithelial cells.

Epithelial Cell Isolation: Rat esophageal tissue was harvested from Fischer 344 rats. Human esophageal tissue was obtained from consenting patients undergoing rigid esophagascopy according to institutionally accepted human subject protocols. Isolated tissues were rinsed well with 4° C. phosphate buffered saline (PBS, Sigma, St. Louis, Mo.). Rat and human esophageal epithelial cells were isolated from tissue samples as follows. Tissue samples were washed liberally in PBS with antibiotics (100 U/ml penicillin G sodium, 100 µg/ml streptomycin sulfate and 0.25 µg/ml amphotericin B obtained from Gibco, Carlsbad, Calif.) and incubated at 4° C. overnight in Dispase (50 caseinolytic units/ml, obtained from BD Biosciences, Bedford, Mass.) plus antibiotics). The following day, the epithelial lining was manually removed from the connective tissue, cut open and treated with 0.05% trypsin in 0.53 mM EDTA (Gibco) for 10 minutes at 37° C. The tissue was subjected to repeated pipetting for an additional 10 minutes, and the trypsin was then neutralized with culture media containing 10% Fetal Bovine Serum (Gibco). The samples were then centrifuged and resuspended in culture media prior to plating. The cells were cultured at 37° C. in 5% $CO_2$ in EpiLife® basal media (Cascade Biologics, Portland, Oreg.) supplemented with 0.03 mM $Ca^{++}$, bovine pituitary extract (0.4%), insulin (5 µg/ml), hydrocortisone (0.5 µg/ml) human epidermal growth factor (0.5 ng/ml), transferring (10 µg/ml), triodothyronine (6.51 ng/ml) and gentamicin/amphotericin-B (Clonetics, Walkersville, Md.). The culture media was changed every 48 hours and the cells were passaged before reaching confluence. The cells were assayed as described below between passage four and passage eleven. To confirm epithelial identity, cultured cells were fixed in −20° C. methanol (Fisher Scientific, Fair Lawn, N.J.), and stained using an anti-cytokeratin 14 antibody (clone LL002, Novocastra Laboratories, United Kingdom). The control consisted of a sample incubated with concentration-matched mouse IgG (Vector Laboratories, Burlingame, Calif.), instead of the primary antibody. Cells were then incubated with a FITC-conjugated rabbit anti-mouse (F0232, Dako, Denmark) and Hoechst 33342 (Sigma) was used as a nuclear counterstain. Cells were imaged using a fluorescent microscope. All cells analyzed (100%) showed strong expression of the basal cell marker, cytokeratin 14, thereby confirming epithelial identity (data not shown).

Tissue Sample Preparation: Rat and Human esophageal tissue samples were obtained as described above and were either snap frozen or paraffin embedded for further analysis. For frozen samples, tissues were snap frozen in Tissue-Tek® O.C.T. compound (obtained from Sakura Finetek, Tokyo, Japan), sectioned using a cryostat (Leica CM 1850, Nussloch, Germany) and stored at −80° C. for histological staining. Samples to be paraffin embedded were fixed with a zinc fixative (2 mM zinc acetate, 37 mM zinc chloride, and 3 mM calcium acetate), paraffin embedded, and sectioned.

Protein Expression Analysis: Immunohistochemistry (IHC) and Western blots were used to analyze Notch-1 and Jagged-1 protein expression in the isolated tissue samples and cultured cells. Primary antibodies used for the analysis included: goat anti-human Notch-1 (sc-6015, Santa Cruz Biotechnology, Santa Cruz, Calif.), goat anti-rat Jagged-1 (AF599, R&D Systems, Minneapolis, Minn.), and rat anti-human Notch-1 (bTan 20, obtained from a hyridoma developed by Spyros Artavanis-Tsakonas, as described in PNAS 92(14):6414-6418 (1995)). The hybridoma developed by Spyros Artavanis-Tsakonas was obtained from the Developmental Studies Hybridoma Band and maintained by the University of Iowa, Iowa City, Iowa.

Western Blot Analysis: Cell lysates were prepared from human esophageal (HEEC) epithelial cells and rat esophageal (REEC) epithelial cells at passage 2 and 7, respectively, that were cultured as described above in culture media containing low (0.03 mM) $Ca^{++}$ and high (1.5 mM) $Ca^{++}$, and protein lysates were collected 72 hours after plating.

Western blot analysis was done using standard techniques. Briefly, protein samples were collected in 2× Laemmili buffer, 15-20 µg of protein was loaded onto a 10% Tris-HCL SDS-PAGE gel. After running the gel, the protein was transferred to a polyvinyldifluoride (PVDF) membrane. For blotting, the membrane was blocked overnight at 4° C. in 10% dry milk in TBS-T (Tris-buffered saline with 0.05% tween-20). The membrane was then incubated for 1 hour at room temperature in the primary antibody. After incubation and rinsing, the membranes were incubated for 1 hour at room temperature with the secondary antibodies, consisting of HRP-conjugate goat anti-mouse and goat anti-rabbit (1:2500, Jackson ImmunoResearch, West Grove, Pa.). The blots were then incubated with the chemiluminescent substrate (Western Lightning, Perkin Elmer, Boston, Mass.). The blots were then placed on x-ray film, exposed and developed.

Immunostaining tissue sections of normal human and rat esophageal tissue with antibodies directed against Notch-1 and Jagged-1 showed strong Notch-1 and Jagged-1 staining in the basal layer, with staining intensity decreasing towards the lumen. Interestingly, the keratin layer of the rat esophagus showed even more intense staining for Notch-1 than did the basal or suprabasal layers (data not shown). The observed regionalized staining patterns of Notch-1 and Jagged-1 suggest a role for Notch pathway signaling in epithelial cell differentiation and stratification.

Cultured epithelial cells derived from the rat and human esophageal tissue were analyzed by Western Blot for protein expression with antibodies directed against Notch-1 and Jagged-1. Western blots of cell lysates from cultured esophageal (HEEC) and rat esophageal (REEC) epithelial cells showed detectable protein expression of Notch-1 and Jagged-1 in both cell types at both low (0.03 mM) and high (1.5 mM) $Ca^{++}$ culture conditions (data not shown).

EXAMPLE 2

This Example describes an effective method for immobilizing Notch ligands onto the surface of a biomaterial.

Recombinant Rat Jagged-1/Fc Chimera: The Rat Jagged-1/Fc chimera used in the following experiments includes Met1 to Asp 1068 from rat Jagged-1 (SEQ ID NO:1), a peptide linker: IEGRMD; fused to a Human IgG1 Fc region (Pro100-Lys 330) with a carboxy-terminal 6× histidine tag (R&D Systems, Catalog No. 599-JG). Rat Jagged-1 is a 1220 amino acid protein that contains a 21 amino acid signal sequence, a 1048 amino acid extracellular region, a 25 amino acid transmembrane domain, and a short, 226 amino acid cytoplasmic domain, as shown in FIG. 1A. Within the large extracellular region (SEQ ID NO:1) is the DSL consensus sequence domain (SEQ ID NO:2) followed by 16 EGF-like repeats and a cysteine-rich region. (Lindsell, C. E. et al, *Cell* 80:909 (1995)). The extracellular domain of Rat Jagged-1 (SEQ ID NO:1) has 98% amino acid identity to human Jagged-1 extracellular domain (SEQ ID NO:3).

Immobilization of Jagged-1: The wells of a tissue culture polystyrene 96 well plate (Corning Costar Acton, Mass.) were incubated overnight at room temperature with recombinant Protein G (50 μg/ml, Zymed Laboratories, San Francisco, Calif.). The wells were rinsed with PBS at room temperature. After rinsing, the wells were blocked with bovine serum albumin (BSA, 10 mg/mL, Sigma) in PBS for 2 hours. Recombinant rat Jagged-1/Fc fusion (R&D Systems, Minneanapolis, Minn.) or human IgG Fc fragment (Jackson ImmunoResearch, West Grove, Pa.) was prepared at 0, 0.01, 0.1, 1 or 10 nM in 0.1% BSA in PBS and added to the wells of the Protein G treated plates for 2 hours. The recombinant Protein G does not have albumin sites and the BSA serves to block regions of the plate not coated with Protein G. Each Protein G molecule is capable of binding to two Fc regions. The sample wells were prepared in triplicates.

ELISA Assay: An antibody-sandwich enzyme-linked immunosorbent assay (ELISA) was used to confirm the presence of Jagged-1/Fc protein bound to the surface of the wells of the tissue culture polystyrene (TCPS) plates. The wells treated with the Jagged-1/Fc protein and Fc control were prepared as described above (with 4% rabbit serum in PBS substituted for BSA) were incubated for 1 hour with goat anti-rat Jagged-1 (1 μg/mL from R&D Systems) diluted in 2% rabbit serum plus PBS. A biotinylated rabbit anti-goat antibody (Vector Laboratories, Burlingame, Calif.) was diluted 1:150 in 2% rabbit serum plus PBS was then added to the wells and incubated for 1 hour. A substrate was added to the wells containing streptavidin/HRP ABC solution (Vector Laboratories), incubated for 45 minutes, rinsed and then a chromogenic solution (1 mg/mL o-phenylenediamine in 0.1M sodium citrate pH 4.5 with 0.015% $H_2O_2$) was added to the wells. The color of the substrate was allowed to develop and the reaction was stopped with the addition of 4.5M sulfuric acid. Absorbance was measured at 490 nm.

Figure 2:
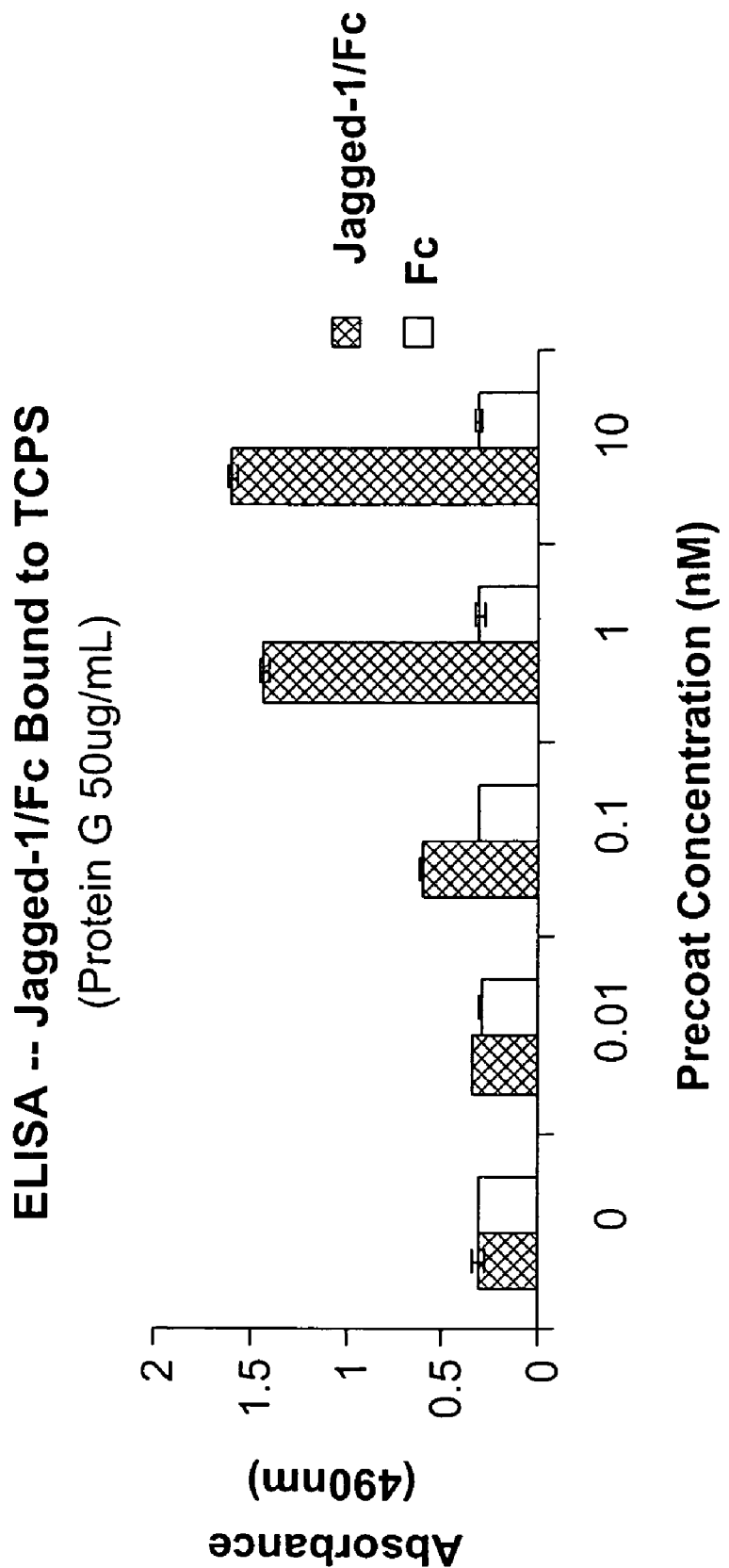
FIG. 2 graphically illustrates that Notch ligand is immobilized to a biomaterial in a dose-dependent manner, as described in Example 2, in accordance with an embodiment of the present invention.

Results: The results of the ELISA are shown in FIG. 2 which graphically shows the concentration of Jagged-1/Fc solution ("precoat concentration") that was added to the wells that were pretreated with Protein G plotted as a function of absorbance (490 nm). As shown in FIG. 2, the amount of absorbance corresponding to the precoat concentration of rJagged-1/Fc is dose dependent, with immobilized rJagged-1/Fc protein detected on the wells at the lowest Jagged-1/Fc precoat concentration (0.1 nM). As further shown in FIG. 2, the assay is specific to Jagged-1/Fc and does not detect the Fc control.

EXAMPLE 3

This Example demonstrates that surface-immobilized Jagged-1/Fc is capable of engaging the Notch Receptor and activating Notch transcription factor dependent expression in epithelial cells with greater potency than soluble Jagged-1 ligand.

Experimental Methods: To confirm that the surface-bound Jagged-1 prepared as described in Example 1 could engage the Notch receptor, a CBF-1 luciferase assay was carried out as described in *J. Biol. Chem.* 276:32022-32030. Briefly described, rat esophageal epithelial cells were transiently transfected in 12-well plates with 900 ng of a reporter plasmid containing four tandem copies of the CBF-1 binding sequence adjacent to a luciferase gene (obtained from L. Liaw, Maine Medical Center Research Institute). The transfection was done using Fugene 6 transfection Reagent (Roche Applied Science, Indianapolis, Ind.) according to the manufacturer's instructions. As a control for transfection efficiency, 100 ng of Renilla SV40 construct (Promega Corporation, Madison, Wis.) was co-transfected with the CBF-1 luciferase construct. The following day, cells were trypsinized and plated in 12 or 24-well tissue culture polystyrene plates for various assays as follows:

Luciferase Assay: For all assays, protein was collected 24 hours after plating and luciferase activity was measured using the Promega Dual-Luciferase® Reported Assay System (Promega, Madison, Wis.).

Results: FIG. 3A shows the amount of Notch specific transcription presented as a ratio of luciferase to Renilla activity to normalize for transfection efficiency, when transfected cells were cultured on plates having various amounts of surface-immobilized Jagged-1/Fc, prepared as indicated in Example 2. The control Fc is shown in parallel. As shown in FIG. 3A, dose-dependent Notch signaling was observed at Jagged/Fc precoat concentrations of 1 nM and 10 nM, whereas no luciferase was expressed in the transfected cells plated on plates bound with Fc only. The increase in signaling was statistically significant compared to controls ($p<0.05$). Repeated experiments have shown that rat esophageal cells transfected with the CSL/luciferase constructed and plated onto plates pretreated with Protein G and 10 nM Jagged-1/Fc, yield a 4 to 10-fold increase in luciferase activity as compared to Fc control plates, as measured at 24 hours (data not shown). Therefore, these results confirmed that the plate-bound Jagged-1/Fc is oriented such that it can engage the Notch receptor expressed on epithelial cells.

Experiments measuring Effects of Soluble Jagged-1/Fc: Cells were plated onto untreated plates and soluble Jagged-1/Fc was added at a 10 mM concentration to the cultured cells 2 hours after plating. In order to measure the effect of calcium concentration on Notch dependent luciferase activity, transfected cells were replated 24 hours after transfection in either media containing high calcium (1.5 mM) or low calcium (0.03 mM).

FIG. 3B shows a comparison of the luciferase/Renilla intensity between cells cultured on untreated plates in the presence of 10 mM soluble Jagged-1/Fc, and cells cultured on plates containing immobilized Jagged-1/Fc (treated with a precoat concentration of 10 mM Jagged-1/Fc) and cultured in the presence of various amounts of $Ca^{++}$. As shown in FIG. 3B, plotted on a logarithmic scale, Notch/CSL signaling was about 10-fold higher in cells exposed to immobilized Jagged-1/Fc than the Fc control. The signaling activity was increased in the presence of high $Ca^{++}$. In contrast, soluble Jagged-1/Fc did not activate Notch/CSL under either low or high calcium concentrations, as compared to the Fc control. Increased Notch signaling in the presence of high calcium levels is in accordance with previous observations (see Rangarajan A. et al., *Embo J.* 20(13):3427-36 (2001)). The dramatic increased activation of Notch signaling in response to immobilized ligand as compared to soluble ligand is a surprising result and may be due to a requirement for the Notch ligand to be properly oriented in order to engage the Notch receptor expressed on epithelial cells.

Figure 3C:
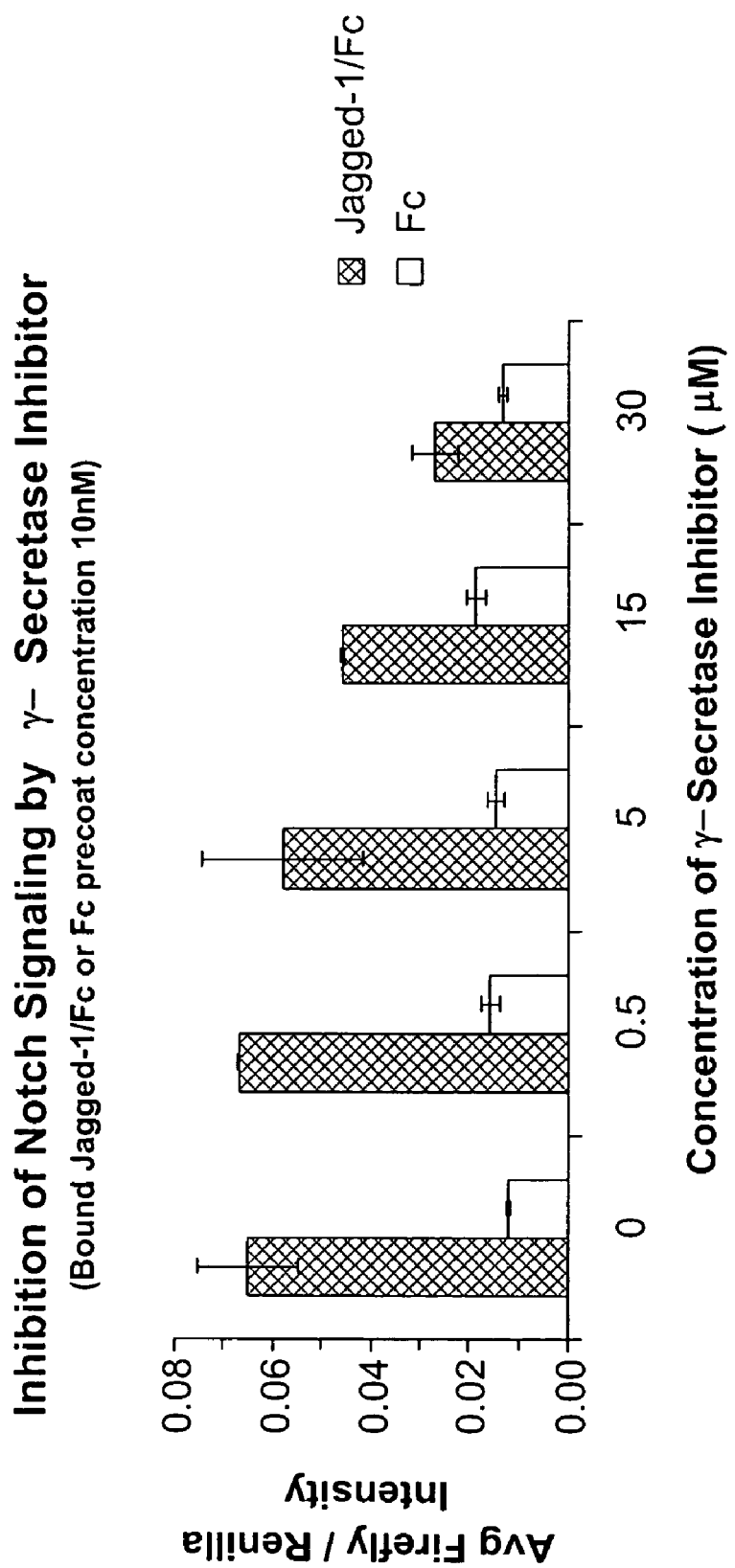
FIG. 3C graphically demonstrates that the Notch signaling shown in FIG. 3B is Notch-specific, as described in Example 3.

In order to confirm that the results shown in FIG. 3B were due to Notch signaling, a control experiment was done in which the cells transfected with the CSL/Luciferase reporter construct were treated with a γ-secretase inhibitor (Cat. #S2188, Sigma) for 15 minutes prior to plating on plates containing surface-immobilized rJagged-1/Fc (10 mM precoat concentration) or an Fc control, prepared as described in Example 2. Lysates were collected after 8 hours. The results shown in FIG. 3C show that signaling by immobilized Jagged-1/Fc was inhibited by the γ-secretase inhibitor in a dose-dependent manner, thereby confirming that the observed luciferase activity was specifically activated via the Notch pathway.

EXAMPLE 4

This Example demonstrates that immobilized Notch ligand is capable of stimulating epithelial cell differentiation and keratinization with greater potency than soluble Notch ligand.

Experimental Methods: Having shown that surface-immobilized Jagged-1 could signal the Notch/CSL pathway as described above in Example 3, the effect of immobilized Notch ligand on epithelial cell differentiation was investigated. Rat esophageal cells obtained as described in Example 1 were cultured at high (1.5 mM) calcium for 72 hours on culture plates treated with various pre-coat concentrations of bound Jagged-1/Fc and Fc controls, prepared as described above in Example 2. After a 72 hour incubation, the cells were harvested, protein was collected in 2× Laemmili buffer and analyzed by Western Blot using the methods described in Example 1, for the expression of involucrin, filaggrin, loricrin and cytokeratin 10, which are all markers of epithelial cell differentiation as described herein in reference to TABLE 1. The following primary antibodies were used: rabbit anti-mouse loricrin (1:1000, Covance, Berkeley, Calif.), mouse anti-human cytokeratin 10 (1:400, clone DE-K10, Dako, Denmark), mouse anti-human involucrin (1:100, clone SY5, LabVision, Fremont, Calif.), rabbit anti-human actin (1:500, I-19, Santa Cruz Biotechology, Santa Cruz, Calif.), and rabbit anti-rat filaggrin (1:1000, gift of Dr. Beverly Dale-Crunk, University of Washington, Seattle, Wash., described in Dale, B. et al., *J. Invest. Dermatol.* 81:90 (1983)).

Figure 4A:
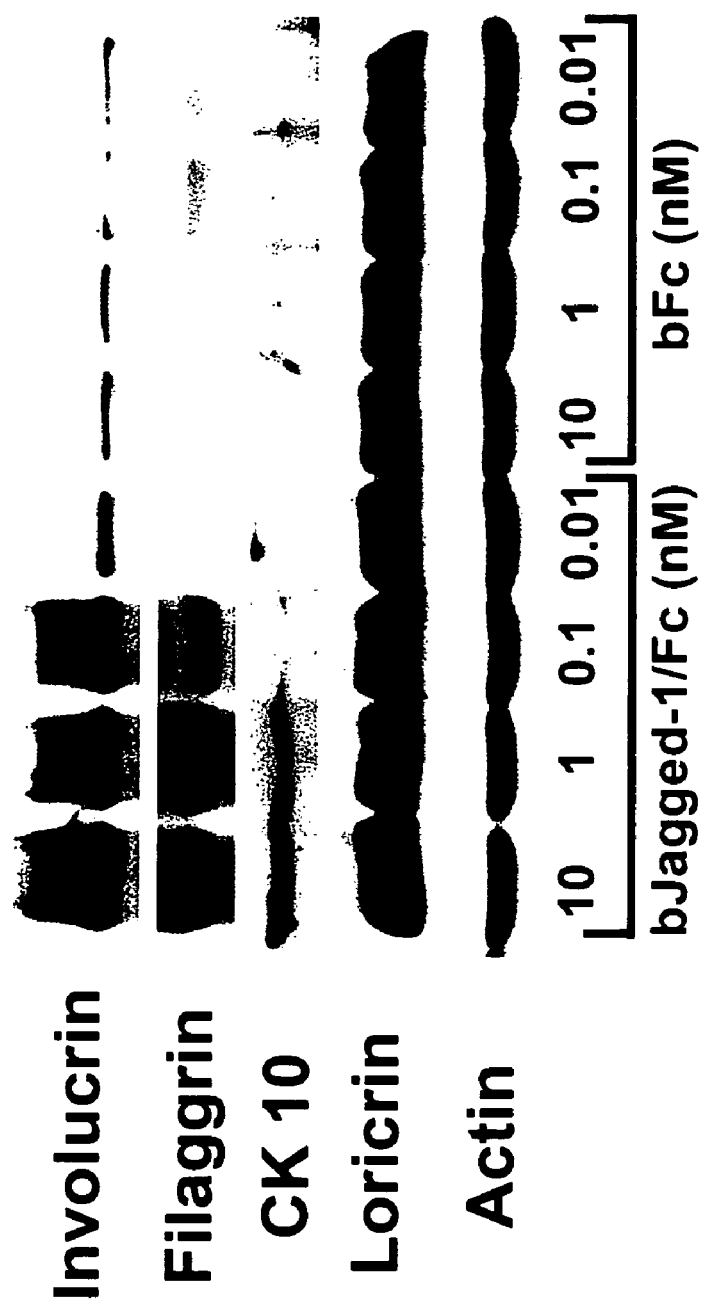
FIG. 4A demonstrates that esophageal cells express differentiation markers after exposure to immobilized Notch ligand, as described in Example 4.
Figure 4B:
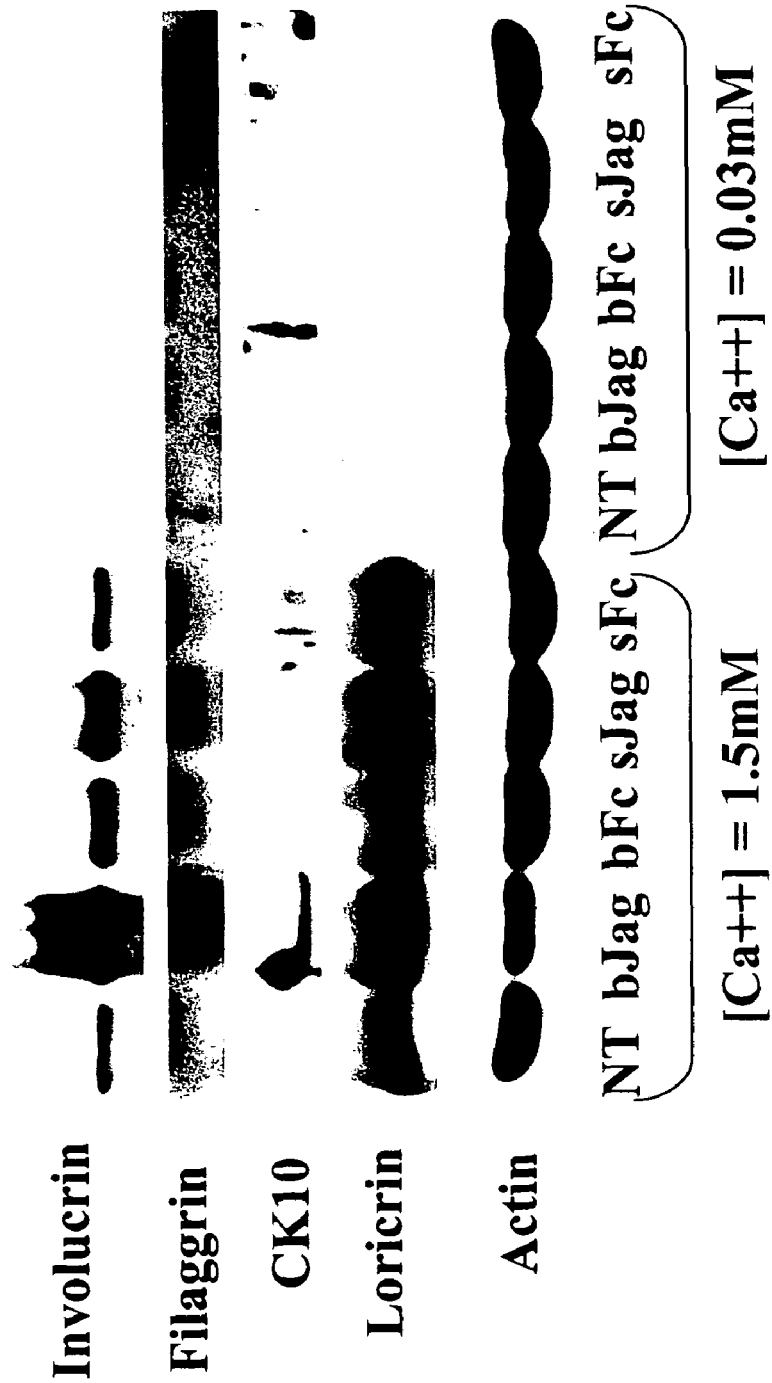
FIG. 4B demonstrates that immobilized Notch ligand stimulates epithelial cell differentiation with greater potency than soluble Notch ligand, as described in Example 4.

The results of the Western blot of REEC cells after 72 hours exposed to immobilized Jagged-1 are shown in FIG. 4A, with Actin included as a control for protein loading. As shown in FIG. 4A, when REEC cells were cultured on plates with immobilized Jagged-1 ligand (precoat concentrations of 0.01, 0.1, 1 and 10 nM) in the presence of 1.5 mM calcium, a marked increase in both intermediate stage (involucrin and cytokeratin 10 (CK10)) and late stage (filaggrin) differentiation markers was observed in comparison to cells cultured on control plates containing immobilized Fc. The expression of cytokeratin 10 gradually increased in response to increasing dosages (0.1 to 10 nM) of immobilized Jagged-1. Involucrin appears to reach a plateau of expression (from 0.1 nM to 10 nM precoat concentration). While Jagged-1 did not appear to influence loricrin expression in comparison to Fc controls, expression of filaggrin expression increased in a dose-dependent response to the presence of immobilized Jagged-1.

In order to compare the effect of immobilized Jagged-1 versus soluble Jagged-1 on the expression of epithelial cell differentiation markers, REEC cells were plated onto plates having immobilized Jagged-1 (precoat 10 nM), or onto untreated plates in the presence of soluble Jagged-1 (10 mM) under both low (0.03 mM) and high (1.5 mM) calcium concentrations. The cells were analyzed by Western Blot for expression of intermediate and late stage epithelial cell differentiation markers using the methods described above, and the results are shown in FIG. 4B. Delivery of Jagged-1 ligand under low calcium conditions resulted in no observable upregulation of differentiaton markers in REEC cells, consistent with the results shown in FIG. 4A. In the presence of high calcium concentration, REEC cells expressed high levels of involucrin, CK10 and filaggrin in response to immobilized Jagged-1, in comparison to lower levels of involucrin, and no expression of filaggrin or CK10 in response to soluble Jagged-1.

Figure 4C:
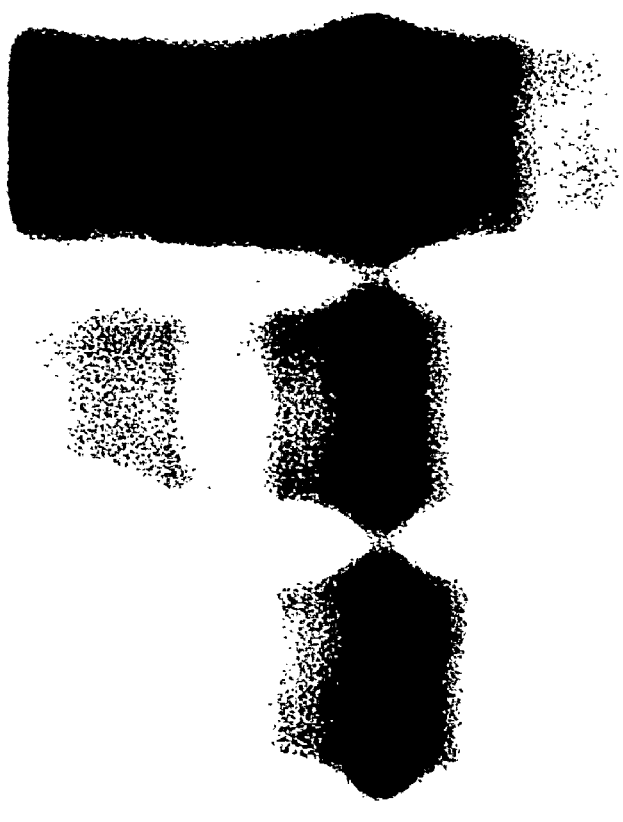
FIG. 4C demonstrates that immobilized Notch ligand stimulates differentiation in human oral keratinocytes, as described in Example 4, in accordance with an embodiment of the present invention.
Figure 5B:
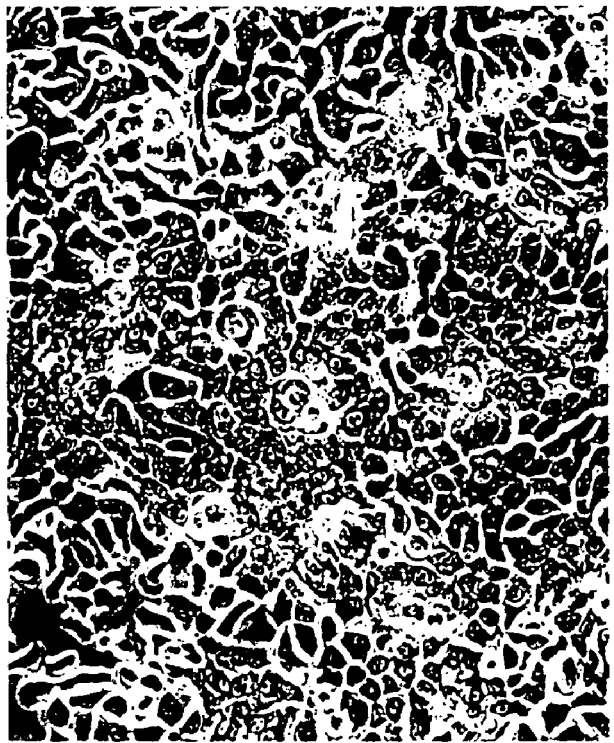
FIG. 5B demonstrates a control experiment showing that undifferentiated rat esophageal epithelial cells in the presence of precoat 0.1 nM Fc immobilized on a culture vessel remain undifferentiated, as described in Example 5.
Figure 5A:
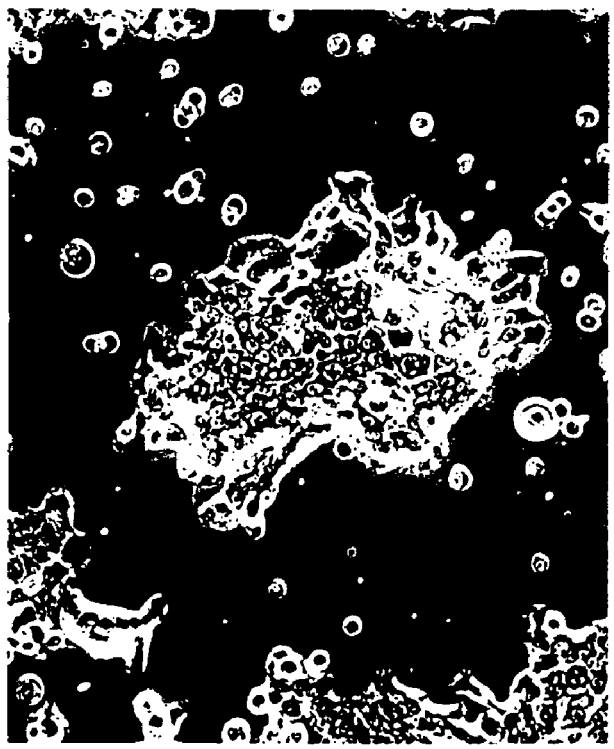
FIG. 5A demonstrates that undifferentiated rat esophageal epithelial cells cultured in the presence of immobilized precoat 0.1 NM Jagged-1/Fc results in a differentiated morphology, as described in Example 5, in accordance with an embodiment of the present invention.
Figure 5D:
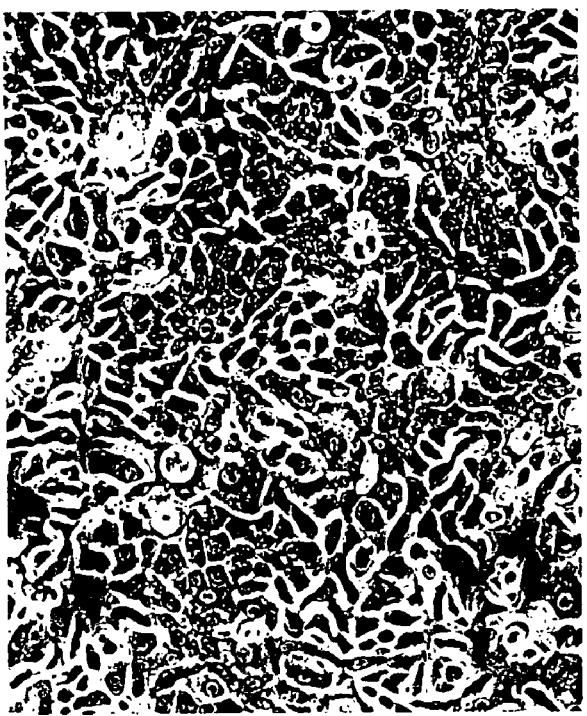
FIG. 5D demonstrates a control experiment, showing that undifferentiated rat esophageal epithelial cells in the presence of precoat 1.0 nM Fc immobilized on a culture vessel remain undifferentiated, as described in Example 5.
Figure 5C:
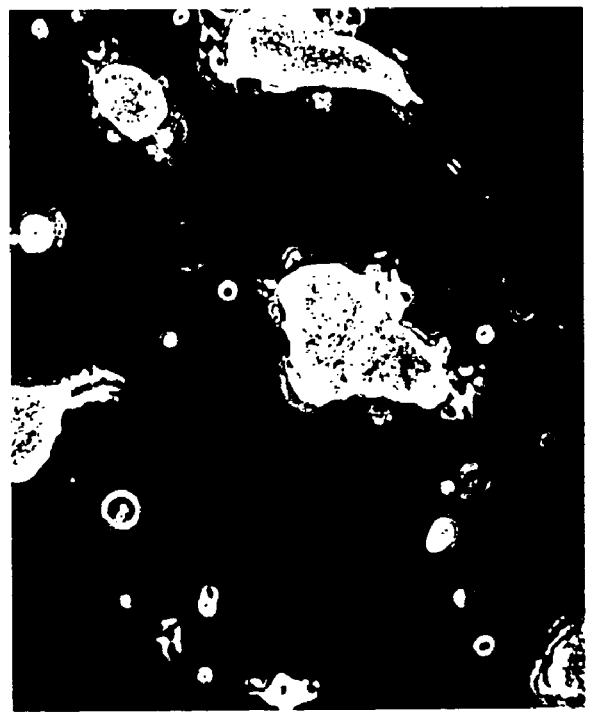
FIG. 5C demonstrates that undifferentiated rat esophageal epithelial cells cultured in the presence of immobilized precoat 1.0 nM Jagged-1/Fc results in a differentiated morphology with cell piling, as described in Example 5, in accordance with an embodiment of the present invention.

In another experiment, Human Oral Keratinocytes isolated from healthy gingival tissue (gift from Beverly A. Dale, Dept. of Oral Biology, University of Washington; see Chung et al., *J. Immunol.* 173:5165-5170 (2004)) were plated onto plates with immobilized Jagged-1 (precoat 10 nM), or Fc control plates (pre-coat 10 nM), and Western Blot analysis for involucrin expression (1:100, clone SY5, LabVision, Fremont, Calif.) was done after 72 hours in culture. The results of this experiment are shown in FIG. 4C. As shown, human cells exposed to immobilized Jagged-1 had increased expression of involucrin, an intermediate stage differentiation marker, as compared to untreated cells, or cells treated with immobilized human Fc receptor alone, consistent with the results shown in rat esophageal cells described above.

In conclusion, these results demonstrate that surface immobilized Jagged-1 is capable of activating the Notch receptor in both rat and human epithelial cells. In addition, the immobilized Notch ligand leads to epithelial differentiation and keratinization in a dose dependent manner. These results further demonstrate that immobilized Jagged-1 provides more potent Notch signaling in epithelial cells than soluble Jagged-1, and that Notch receptor activation via immobilized Jagged-1 upregulates intermediate and late stage differentiation markers in epithelial cells.

EXAMPLE 5

This Example demonstrates that undifferentiated epithelial cells plated on plates containing immobilized Jagged-1 are induced to differentiate and form tight clusters and layers consistent with differentiated epithelial cells morphology.

Experimental Methods: Jagged-1/Fc and control Fc was immobilized to the surface of either transwell inserts (12 mm diameter, 0.4 uM pore size, polyester membrane, Corning Co-star, Acton, Mass.), or 6-well tissue culture polystyrene plates (Corning), as described above in Example 2. Rat esophageal epithelial cells (REEC cells) were obtained as described in Example 1. The REEC cells were plated at 25,000 cells/cm$^2$ (6-well plates, passage 7) or 45,000 cells/cm$^2$ (for transwell, passage 10) onto plates containing immobilized Jagged-1/Fc and Fc only at precoat concentrations of 0.1 nM, 1 nM and 10 nM. The media was changed every 48 hours. At 48 hours, cells plated in 6-well plates were imaged using phase microscopy. At 72 hours, the transwell inserts were rinsed with PBS and fixed in 10% formalin (Fisher) for 1 hour at room temperature. After fixation, the inserts were rinsed with PBS, removed from the support with an 8 mm biopsy punch, and processed for paraffin embedding. Slides were prepared and stained with hematoxylin and eosin (H&E). Hematoxylin stains negatively charged nucleic acids (nuclei & ribosomes) blue. Eosin stains proteins pink.

Results: The results are shown in FIGS. 5A-D. As shown, REEC cells plated in 6-well plates onto immobilized Jagged-1/Fc precoat 0.1 nM, shown in FIG. 5A and at Jagged-1/Fc precoat 1 nM, shown in FIG. 5B form tight clusters and pile together after 48 hours in culture, consistent with epithelial cell differentiation. Cells plated onto immobilized Jagged-1/Fc precoat 10 nM showed similar morphology (data not shown). No differentiation morphology was observed in control Fc plates at 0.1 nM, shown in FIG. 5B, or at 1 nM, shown in FIG. 5D, or at 10 nM (data not shown).

Figure 6A:
FIG. 6A demonstrates a histological cross-section of the differentiated epithelial cells cultured in the presence of immobilized precoat 10 nM Jagged-1/Fc, showing the presence of at least five layers of cells in tight clusters, as described in Example 5, in accordance with an embodiment of the present invention.
Figure 6B:
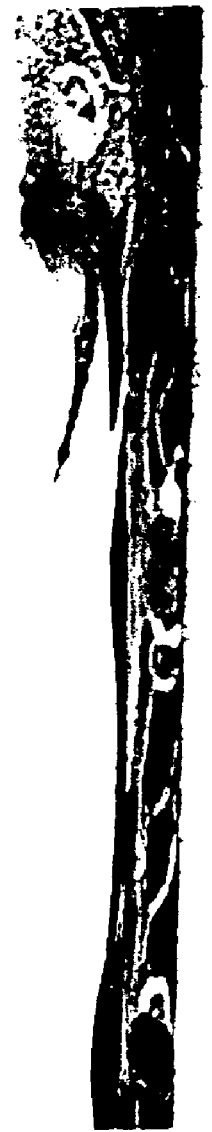
FIG. 6B demonstrates a histological cross-section of the cells in the control culture grown on immobilized precoat 10 nM Fc, showing from one to two layers of cells, as described in Example 5.

As further shown in FIG. 6A, REEC cells plated in the transwell insert on Jagged-1/Fc precoat 10 nM, rapidly stratified, forming up to five layers of cells in tight clusters, as compared to the two layers formed after culture on Fc control precoat 10 nM plates, shown in FIG. 6B.

EXAMPLE 6

This example demonstrates the use of a biomaterial comprising immobilized Notch ligand for esophageal tissue development on a synthetic scaffold.

Experimental Rationale: Esophageal cancer, in addition to other tracheoesophageal disorders, is often so debilitating that it requires esophageal replacement for patient survival. Currently, natural substrates prepared from transected stomach, jejunum and colon are utilized with some effectiveness in these patients. However, complications including leakage, stricture, elongation and malnutrition frequently occur. A viable, tissue-engineered esophageal construct generated on a scaffold would overcome these complications.

Methods: In an effort to improve esophageal tissue development on synthetic scaffolds, a study was done to examine the use of the Notch ligand Jagged-1 as a cell instructive signal on synthetic cell instructive matrices. Jagged-1 ligand was immobilized onto the surface of a biomaterial using an affinity immobilization scheme as described in EXAMPLE 2 Rat esophageal cells were isolated as described above in EXAMPLE 1 and tested on the biomaterial for Notch signaling and morphology.

Results: The results demonstrated that the immobilized Jagged-1 was able to signal the Notch pathway via the Notch/CBF-1, as described above in EXAMPLE 3. Further, immobilized Jagged-1 induced both intermediate and late-stage differentiation markers as measured by involucrin, filaggrin and cytokeratin 10 expression. In contrast, soluble Jagged-1 added to the cultures containing the synthetic scaffolds only weakly stimulated epithelial differentiation (data not shown).

Summary: These results demonstrate that immobilization of a Notch ligand on a biomaterial such as a synthetic tissue scaffold provides a powerful technique with which to control epithelial cell behavior, and has applications in tissue engineering, wound healing and medical device, such as transcutaneous devices.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A partially implantable medical device, comprising at least one epithelial tissue contacting surface, wherein the epithelial tissue contacting surface comprises a layer of a biomaterial, wherein the biomaterial comprises a plurality of immobilized Notch ligand molecules, wherein each immobilized Notch ligand:
   (i) comprises the human Delta, Serrate, Lag-s ("DSL") sequence set forth as SEQ ID NO:4;
   (ii) binds to a Notch receptor; and
   (iii) promotes differentiation of one or more epithelial cells in the contacted epithelial tissue, wherein the carboxyl-terminal end of each of the plurality of Notch ligand molecules is immobilized to the biocompatible epithelial tissue contacting surface of the biomaterial.

2. The partially implantable device of claim 1, wherein the device is an in-dwelling.

3. The partially implantable medical device of claim 1, wherein the biomaterial further comprises at least one adhesive protein that promotes at least one of epithelial cell migration or attachment to the surface of the biomaterial.

4. The partially implantable medical device of claim 1, wherein the plurality of Notch ligand molecules each further comprise a carboxyl terminal IgG Fc binding domain.

5. The partially implantable medical device of claim 1, wherein the device is a transcultaneous biosensor.

* * * * *